US006686385B2

(12) United States Patent
Saulnier et al.

(10) Patent No.: US 6,686,385 B2
(45) Date of Patent: Feb. 3, 2004

(54) ANHYDRO SUGAR DERIVATIVES OF INDOLOCARBAZOLES

(75) Inventors: Mark G. Saulnier, Higganum, CT (US); Edward H. Ruediger, Greenfield Park (CA); Neelakantan Balasubramanian, Madison, CT (US); David Bertil Frennesson, Naugatuck, CT (US); Mikael Mahler, Outremont (CA); Kurt Zimmermann, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/431,221

(22) Filed: May 7, 2003

(65) Prior Publication Data

US 2003/0220387 A1 Nov. 27, 2003

Related U.S. Application Data

(62) Division of application No. 09/965,069, filed on Sep. 27, 2001, now Pat. No. 6,610,727.
(60) Provisional application No. 60/238,696, filed on Oct. 6, 2000.

(51) Int. Cl.[7] .......................... A61K 31/55; A61P 43/00; C07D 498/22
(52) U.S. Cl. ........................................ 514/410; 548/416
(58) Field of Search .......................... 548/416; 514/410

(56) References Cited

U.S. PATENT DOCUMENTS

| | | |
|---|---|---|
| 4,487,925 A | 12/1984 | Nettleton, Jr. et al. |
| 4,552,842 A | 11/1985 | Nettleton, Jr. et al. |
| 4,567,143 A | 1/1986 | Matson |
| 4,785,085 A | 11/1988 | Kaneko et al. |
| 5,043,335 A | 8/1991 | Kleinschroth et al. |
| 5,407,940 A | 4/1995 | Bisagni et al. |
| 5,468,849 A | 11/1995 | Lam et al. |
| 5,468,872 A | 11/1995 | Glicksman et al. |
| 5,475,110 A | 12/1995 | Hudkins et al. |
| 5,478,813 A | 12/1995 | Okaniski et al. |
| 5,498,611 A | 3/1996 | Bisagni et al. |
| 5,589,365 A | 12/1996 | Kojiri et al. |
| 5,618,809 A | 4/1997 | Barrabee et al. |
| 5,668,271 A | 9/1997 | Kojiri et al. |
| 5,674,867 A | 10/1997 | Tamaoki et al. |
| 6,037,468 A | 3/2000 | Wood et al. |

FOREIGN PATENT DOCUMENTS

| | | |
|---|---|---|
| EP | 0 450 327 A1 | 10/1991 |
| EP | 0602597 A2 | 12/1993 |
| EP | 0545195 B1 | 11/1995 |
| EP | 1101770 A | 5/2001 |
| HU | 203758 B | 9/1991 |
| HU | 211254 B | 11/1995 |
| HU | 217611 B | 3/2000 |
| WO | WO 89/07105 | 10/1989 |
| WO | WO 95/30682 | 11/1995 |
| WO | WO 96/04293 | 2/1996 |
| WO | WO 96/11933 | 4/1996 |
| WO | WO 98/07433 | 2/1998 |
| WO | WO 99/02532 | 1/1999 |

OTHER PUBLICATIONS

B. B. Shankar, S. W. McCombie, *Tetrahedron Lett.* (1994), 35: 3005.
B. M. Stolz, J. L. Wood, *Tetrahedron Lett.* (1995), 36: 8543.
J. Anizon, et al., *Bioorg. & Med. Chem.* (1998), 6: 1597.
S. W. McCombie, et al., *Bioorg. & Med. Chem. Lett.* (1993), 8: 1537.
C. Bailly, et al., *Biochem.*, (1997), 36: 3917.
D. Von Hoff, et al., *Cancer Chemother., Pharmacol.* (1994), 34 (suppl): S41.
T. Yoshinari, et al., *Cancer Research*, (1993), 53: 490.
T. Yoshinari, et al., *Cancer Research*, (1995), 55: 1310.
D.A. Scudiero, et al, *Cancer Research*, (1988), 48: 4827.
E.R. Pereira, et al, *J. Med. Chem.*, (1996), 39: 4471.
Greene and Wuts, Protective Groups in Organic Synthesis, 2nd Ed., John Wiley and Sons and McOmie, New York, 1991.
J. L. Wood, et al., *J. Am. Chem. Soc.* (1995), 117:10413.
J. T. Link, et al., *J. Am. Chem. Soc.* (1996), 118: 2825.
R. Kobayoshi, et al., *J. Am. Chem. Soc.* (1999), 121: 6501.
A. Mazur and G. Hiler, *J. Org. Chem.* (1997), 62: 4771.
K. Nowak, et al., *Roczniki Chem.*, (1969), 43: 1953.
M. Gallant, et al., *J. Org. Chem.*, (1993), 58: 343.
M.S. Motawia, et al., *J. Carbohydrate Chemistry*, (1995), 14(9): 1279.
Halcomb and Danishefsky, *J. Amer Chem. Soc.*, (1989) 111: 6661.
Nicolaou et al, *J. Amer. Chem. Soc.*, (1989) 111: 6666.
S. F. Vice, et al., *Bioorg. Med. Chem. Lett.* (1994), 4: 1333.
T. Hayashi, et al., *Bioorganic And Medicinal Chemistry*, (1997), 5(3): 497.
Weinreb, et al., *Heterocycles* (1984), 21: 309.
Y.–H. Hsiang, et al, *J. Biol. Chem.*, (1985), 260(27): 14873.
Gonzalez, et al., *Farmacia Clinica* (1997), 14: 250.
Long, et al., *American Association for Cancer Research Proceedings* (1997), 38: 75.
Madden, et al., *Cancer Research* (1992), 52: 525.
O'Connor, et al., *Cancer Communications* (1990), 2: 395.
Pollack, et al., *Molecular Pharmacology* (1999), 56: 185.
Prudhomme, M., *Current Medicinal Chemistry* (2000), 7: 1189.
B. B. Shankar et al., *Tetrahedron Lett.* (1994), 35: 3005.

(List continued on next page.)

*Primary Examiner*—Joseph K. McKane
*Assistant Examiner*—Andrea D. Small
(74) *Attorney, Agent, or Firm*—Shah Makujina; Kenneth W. Peist

(57) ABSTRACT

The present invention concerns novel sugar derivatives of indolocarbazoles and pharmaceutical formulations thereof which exhibit topoisomerase-I activity and are useful in inhibiting the proliferation of tumor cells.

24 Claims, No Drawings

OTHER PUBLICATIONS

B. M. Stolz et al., *Tetrahedron Lett.* (1995), 36: 8543.
J. Anizon et al., *Bioorg. & Med. Chem.* (1998), 6: 1597.
S.W. McCombie et al., *Bioorg. & Med. Chem. Lett.* (1993), 8: 1537.
C. Bailly et al, *Biochemistry* (1997), 36: 3917.
D. Von Hoff et al., *Cancer Chemother., Pharmacol.* (1994), 34 (suppl): S41.
T. Yoshinari et al., *Cancer Research* (1993), 53: 490.
T. Yoshinari et al., *Cancer Research* (1995), 55: 1310.
D.A. Scudiero et al., *Cancer Research* (1988), 48: 4827.
E.R. Pereira et al., *J. Med. Chem.* (1996), 39: 4471.
J. L. Wood et al., *J. Am. Chem. Soc.* (1995), 117: 10413.
J. T. Link et al., *J. Am. Chem. Soc.* (1996), 118: 2825.
R. Kobayashi et al., *J. Am. Chem. Soc.* (1999), 121: 6501.
A. Mazur et al., *J. Org. Chem.* (1997), 62: 4471.
K. Nowak et al., *Roczniki Chem.* (1996), 43: 1953.
M. Gallant et al., *J. Org. Chem.* (1993), 58: 343.
M.S. Motawia et al., *J. Carbohydrate Chemistry* (1995), 14(9): 1279.
R.L. Halcomb et al., *J. Amer. Chem. Soc.* (1989), 111: 6661.
Nicolaou et al., *J. Amer. Chem. Soc.* (1989), 111: 6666.
S. F. Vice et al., *Bioorg Med. Chem. Lett.* (1994), 4: 1333.
T. Hayashi et al., *Bioorganic And Medicinal Chemistry* (1997), 5(3): 497.
Weinreb et al., *Heterocycles* (1984), 21: 309.
Y.–H. Hsiang et al., *J. Biol. Chem.* (1985), 260(27): 14873.

ANHYDRO SUGAR DERIVATIVES OF INDOLOCARBAZOLES

RELATED APPLICATIONS

This application is a Divisional Application of U.S. patent application Ser. No. 09/965,069, filed on Sep. 27, 2001, now U.S. Pat. No. 6,610,727, which claims priority benefit under Title 35 §119(e) of U.S. Provisional Application No. 60/238,696, filed Oct. 6, 2000, the contents of which are herein incorporated by reference.

FIELD OF THE INVENTION

The present invention describes sugar derivatives of indolocarbazoles which exhibit topoisomerase-I activity and are useful in inhibiting the proliferation of tumor cells.

BACKGROUND

Topoisomerases are vital nuclear enzymes which function to resolve topological dilemmas in DNA, such as overwinding, undewinding and catenation, which normally arise during replication, transcription and perhaps other DNA processes. These enzymes allow DNA to relax by forming enzyme-bridged strand breaks that act as transient gates or pivotal points for the passage of other DNA strands. Topoisomerase-targeting drugs appear to interfere with this breakage-reunion reaction of DNA topoisomerases. In the presence of topoisomerase active agents, an aborted reaction intermediate termed a 'cleavable complex' accumulates and results in replication/transcription arrest, which ultimately leads to cell death. The development of topoisomerase I active agents therefore offers a new approach to the multi-regimental arsenal of therapies currently used in the clinic for the treatment of cancer.

An article in *Cancer Chemother. Pharmacol* [1994, 34 (suppl): S 41–S 45] discusses topoisomerase I active compounds that have been found to be effective clinical anti-tumor agents. Structurally these clinical candidates are related to the alkaloid camptothecin.

Indolo[2,3-a]carbazole alkaloids such as rebeccamycin (U.S. Pat. No. 4,487,925 and U.S. Pat. No. 4,552,842) and its water-soluble, clinically-active analog, 6-(2-diethylaminoethyl)rebeccamycin (U.S. Pat. No. 4,785,085), are useful antitumor agents which target DNA. Furthermore, fluoroindolocarbazoles have been disclosed in WO 98/07433 to act as antineoplastic agents with topoisomerase I inhibitory activity.

Indolo[2,3-a]carbazole derivatives related to the Rebeccamycin class are disclosed (EP Appl. 0 545 195 B1 and 0,602,597 A2; *Cancer Research* 1993, 53, 490–494; *ibid* 1995, 55, 1310–1315) and claimed to exhibit anti-tumor activity. However, the major mechanism of action of these derivatives may not be like camptothecin, which acts as a topoisomerase I poison. Other indolocarbazoles related to those mentioned above are disclosed in WO 95/30682 and are claimed to exhibit anti-tumor activity.

Hudkins, et al. disclosed a series of fused pyrrolocarbazoles (WO 96/11933 and U.S. Pat. No. 5,475,110) and showed in vitro biological data such as inhibition of neuronal choline acetyltransferase (ChAT) and protein kinase C (PKC) inhibition for some compounds. U.S. Pat. No. 5,468,849 discloses certain fluororebeccamycin analogs as useful antitumor agents, along with a process for their production by fluorotryptophan analog feeding of a rebeccamiycin-producing strain of *Saccharothrix aerocolonigenes*, particularly *Saccharothrix aerocolonigenes* C38,383-RK2 (ATCC 39243). Glicksman, et al. disclose indolocarbazole alkaloids (U.S. Pat. No. 5,468,872) which are different in structure from those of the present invention. Kojiri, et al. disclose indolopyrrolocarbazoles having a dissacharide substituent (WO 96/04293) which are not related to the anhydrosugar indolocarbazoles. Weinreb, et al. (*Heterocycles* 1984, 21, 309) and Kleinschroth, et al. (U.S. Pat. No. 5,043,335) have disclosed indolopyrrolocarbazole derivatives with a bridging furan moiety and McCombie, et al. (*Bioorg. Med. Chem. Lett.* 1993, 3, 1537) have reported a more functionalized bridged furan. Similarly, Wood, et al. have reported the total synthesis of (+)-K252a (*J. Am. Chem. Soc.* 1995, 117, 10413), a related, naturally-occuring indolocarbazole alkaloid which has demonstrated PKC inhibitory activity.

Danishefsky, et al., during the course of their first total synthesis of staurosporine (*J. Am. Chem. Soc.* 1996, 118, 2825), describe the synthesis of an intermediate N12, N13-bridged indolopyrrolocarbazole. Indolocarbazole derivatives with the nitrogens linked by a three-atom bridge have been reported to be potent PKC inhibitors. (S. F. Vice, et al. *Bioorg. Med. Chem. Lett.* 1994, 4, 1333). The synthesis of simple indolocarbazole derivatives with C1', C-5'-bridging or C1', C3'-bridging glycosides have also been reported in the literature (B. M. Stolz, J. L. Wood *Tetrahedron Lett.* 1995, 36, 8543, B. B. Shankar, S. W. McCombie *Tetrahedron Lett.* 1994, 35, 3005, respectively). Prudhomme, et al. disclose a series of antitumor indolocarbazoles derived from rebeccamycin which exhibit a carbohydrate attached to the two indole nitrogens, and reported their cytotoxicity and their topoisomerase I and PKC inhibitory activities to be in the millimolar to micromolar range (*Bioorg. Med. Chem.* 1998, 6,1597). There is yet a need for novel and potent cytotoxic compounds useful for inhibiting topoisomerase I activity.

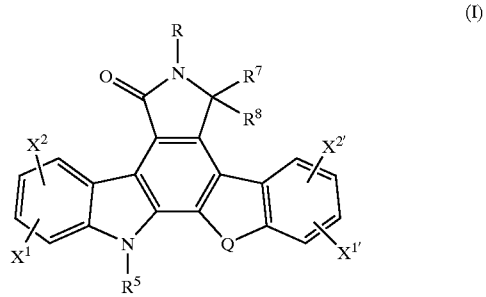

(I)

SUMMARY OF THE INVENTION

Thus according to a first embodiment of the first aspect of the present invention are provided compounds of Formula (I) and pharmaceutically acceptable salts and solvates thereof, useful for inhibiting topoisomerase I and the proliferation of tumor cells wherein:

R is hydrogen, OH, $OC_{1-7}$alkyl, $NH_2$, $N(C_{1-3}alkyl)_2$ or $C_{1-7}$alkyl, wherein said $C_{1-7}$alkyl is optionally substituted with one or more substituents selected from the group consisting of halogen, CN, $OR^9$ and $NR^9R^{10}$;

Q is O, S, $CH_2$ or $NR^{5a}$;

$R^5$ and $R^{5a}$ are each independently selected from the group consisting of hydrogen, Formula (A), Formula (B), Formula (C) and Formula (D):

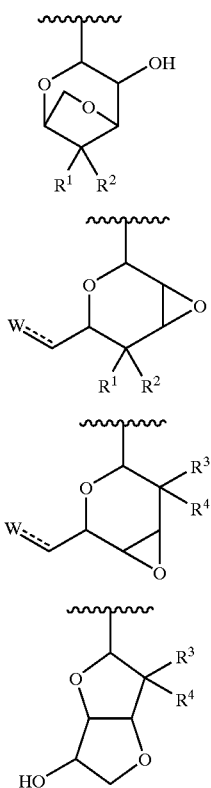

provided that
if Q is NR$^{5a}$, then either R$^5$ or R$^{5a}$ must be hydrogen;
R$^1$, R$^2$, R$^3$ and R$^4$ are each independently selected from the group consisting of hydrogen, C$_{1-7}$alkyl, C$_{3-7}$cycloalkyl, halogen, azido, NR$^9$R$^{10}$, NHC(O)NR$^9$R$^{10}$, NHC(O)OR$^9$, C(O)OR$^9$, SR$^9$ and OR$^9$, wherein said C$_{1-7}$alkyl is optionally substituted with one or more substituents selected from the group consisting of halogen, CN, OR$^9$, SR$^9$ and NR$^9$R$^{10}$;
or R$^1$ and R$^2$ together form =N—OH, =O or —NR$^9$R$^{10}$;
or R$^3$ and R$^4$ together form =N—OH, =O or —NR$^9$R$^{10}$;
W is selected from the group consisting of hydrogen, C$_{1-7}$alkyl, C$_{3-7}$cycloalkyl, halogen, azido, NR$^9$R$^{10}$, NHC(O)NR$^9$R$^{10}$, NHC(O)OR$^9$, N—OH, O and OR$^9$, wherein said C$_{1-7}$alkyl is optionally substituted with one or more substituents selected from the group consisting of halogen, CN, OR$^9$ and NR$^9$R$^{10}$;
R$^7$ and R$^8$ are independently OH or H or together form =O;
R$^9$ and R$^{10}$ are independently selected from the group consisting of hydrogen, C$_{1-7}$alkyl and C$_{3-7}$cycloalkyl, wherein said C$_{1-7}$alkyl is optionally substituted with one or more substituents selected from the group consisting of halogen, CN, OH, O—C$_{1-7}$alkyl, NH$_2$ and N(C$_{1-3}$alkyl)$_2$; or
R$^9$ and R$^{10}$ together with the nitrogen atom to which they are attached form a non-aromatic 5–8 membered heterocycle containing one or two of the same or different heteroatoms selected from the group consisting of O, N and S; and
X$^1$, X$^{1'}$, X$^2$ and X$^{2'}$ are independently selected from the group consisting of hydrogen, halogen, cyano, OR$^9$, —CF$_3$, alkylcarbonyl, C-$_{1-7}$alkyl, nitro, NR$^9$R$^{10}$, SR$^9$ and C(O)OR$^9$; wherein said C$_{1-7}$alkyl is optionally substituted with one or more substituents selected from the group consisting of halogen, CN, OR$^9$, SR$^9$ and NR$^9$R$^{10}$.

According to another embodiment of the first aspect of the present invention are provided compounds of Formula (I) wherein R$^{5a}$ is not H.

According to another embodiment of the first aspect of the present invention are provided compounds of Formula (I) wherein R$^{5a}$ is formula (C) or (A).

According to another embodiment of the first aspect of the present invention are provided compounds of Formula (I) wherein R$^5$ is formula (A).

According to another embodiment of the first aspect of the present invention are provided compounds of Formula (I) wherein R$^5$ is formula (B).

According to another embodiment of the first aspect of the present invention are provided compounds of Formula (I) wherein R$^5$ is formula (C).

According to another embodiment of the first aspect of the present invention are provided compounds of Formula (I) wherein R$^5$ is formula (D).

According to another embodiment of the first aspect of the present invention are provided compounds of Formula (I) wherein Q is NR$^{5a}$ and R$^{5a}$ is H or wherein Q is S.

According to another embodiment of the first aspect of the present invention are provided compounds of Formula (I) wherein R is H, OH or NH$_2$.

According to another embodiment of the first aspect of the present invention are provided compounds of Formula (I) wherein R is H.

According to another embodiment of the first aspect of the present invention are provided compounds of Formula (I) wherein R$^7$ and R$^8$ together are =O.

According to another embodiment of the first aspect of the present invention are provided compounds of Formula (I) wherein X$^{2'}$ and X$^2$ are each F and X$^1$ and X$^{1'}$ are each H.

According to another embodiment of the first aspect of the present invention are provided compounds of Formula (I) wherein X$^2$ is F and X$^{2'}$, X$^1$ and X$^{1'}$ are each H.

According to another embodiment of the first aspect of the present invention are provided compounds of Formula (I) wherein X$^{2'}$ is F and X$^2$, X$^1$ and X$^{1'}$ are each H.

According to another embodiment of the first aspect of the present invention are provided compounds of Formula (I) wherein X$^{2'}$, X$^2$, X$^1$ and X$^{1'}$ are each F.

According to another embodiment of the first aspect of the present invention are provided compounds of Formula (I) wherein X$^{2'}$ and X$^2$ are each H and X$^1$ and X$^{1'}$ are each F.

According to another embodiment of the first aspect of the present invention are provided compounds of Formula (I) wherein R$^1$, R$^2$ R$^3$ and R$^4$ are independently selected from the group consisting of H, F and OR$^9$ wherein R$^9$ is H.

According to another embodiment of the first aspect of the present invention are provided compounds of Formula (I) wherein W is fluorine.

According to another embodiment of the first aspect of the present invention are provided compounds of Formula (I) wherein the bond attaching R$^5$ to N is in the β designation when R$^5$ is not hydrogen.

According to another embodiment of the first aspect of the present invention are provided compounds of Formula (I) wherein the bond attaching R$^{5a}$ to N is in the β designation when R$^{5a}$ is not hydrogen.

According to another embodiment of the first aspect of the present invention are provided compounds of Formula (I)

wherein the bond attaching $R^5$ to N is in the α designation when $R^5$ is not hydrogen.

According to another embodiment of the first aspect of the present invention are provided compounds of Formula (I) wherein the bond attaching $R^{5a}$ to N is in the α designation when $R^{5a}$ is not hydrogen.

Other embodiments of the first aspect of the present invention provide compounds of Formula (I) comprising two or more of the above embodiments of the first aspect suitably combined.

Embodiments of a second aspect of the present invention provide a method for inhibiting tumor growth in a mammalian host which comprises the administration to said host of a tumor-growth inhibiting amount of a compound of the present invention as defined herein.

Embodiments of a third aspect of the present invention provide a method for inhibiting tumor growth in a mammalian host, particularly a human host, comprising the administration to said host of a tumor-growth inhibiting amount of a pharmaceutical formulation of a compound of the present invention as defined herein.

Other embodiments and aspects of the invention will be apparent according to the description provided below.

DETAILED DESCRIPTION OF THE INVENTION

The description of the invention herein should be construed in congruity with the laws and principals of chemical bonding. An embodiment or aspect which depends from another embodiment or aspect, will describe only the variables having values and provisos that differ from the embodiment or aspect from which it depends. Thus, for example, an embodiment which reads "the compound of formula (I) according to the $n^{th}$ aspect of the invention, wherein W is C" should be read to include all remaining variables with values defined in the $n^{th}$ aspect and should be read to further include all the provisos, unless otherwise indicated, pertaining to each and every variable in the $n^{th}$ aspect. Where a variable is defined as having a value of zero, it is understood that the bond attached to said variable should be removed. For example, if n=0 and R—X—$V_n$ wherein n can be 0 or 1, then it is understood that the structure described is R—X not R—X—.

The numbers in the subscript after the symbol "C" define the number of carbon atoms a particular group can contain. For example "$C_{1-7}$alkyl" means a straight or branched saturated carbon chain having from one to seven carbon atoms including without limitation groups such as methyl, ethyl, n-propyl, isopropyl, n-butyl, sec-butyl, isobutyl, t-butyl, n-pentyl, sec-pentyl, isopentyl, n-hexyl and n-heptyl. The term "halogen" includes fluoro, chloro, bromo and iodo.

It is to be understood that the present invention includes any and all possible stereoisomers, geometric isomers, diastereoisomers, enantiomers, anomers and optical isomers, unless a particular description specifies otherwise.

The compounds of this invention can exist in the form of pharmaceutically acceptable salts. Such salts include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group can exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those of ordinary skill in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

One aspect of the present invention involves administration of the compounds of the present invention, or pharmaceutically acceptable salts or solvates thereof, to a mammal implanted with a tumor or susceptible to cancer formation. In general the compound would be given in a dose range of from about 0.01 mg/kg to about the MTD (maximum tolerated dose). The dosage and dosage regimen and scheduling of a compounds of the present invention must in each case be carefully adjusted, utilizing sound professional judgment and considering the age, weight and condition of the recipient, the route of administration and the nature and extent of the cancer disease condition. The term "systemic administration" as used herein refers to oral sublingual, buccal, transnasal, transdermal, rectal, intramascular, intravenous, intraventricular, intrathecal, and subcutaneous routes. In accordance with good clinical practice, it is preferred to administer the instant compounds at a concentration level which will produce effective beneficial effects without causing any harmful or untoward side effects.

Synthesis

Procedures for the preparation of compounds of the present invention compounds are illustrated in Schemes 1–4:

Scheme I:

Example 1:

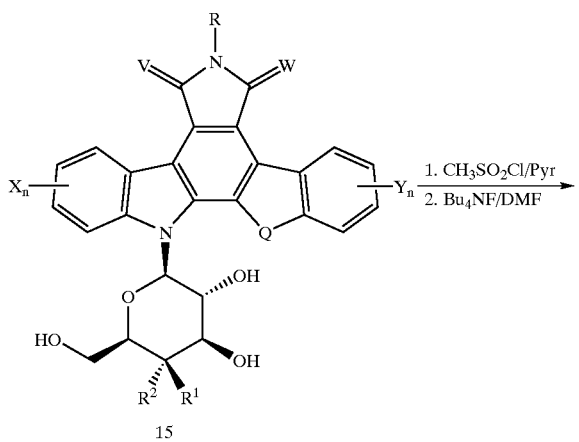

15

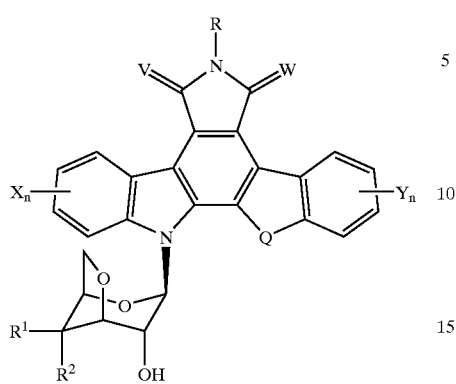
Example 2:
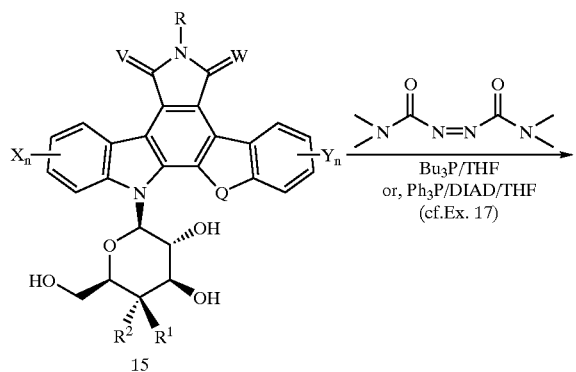
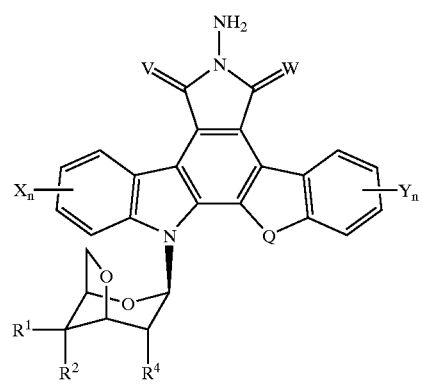
Example 4:
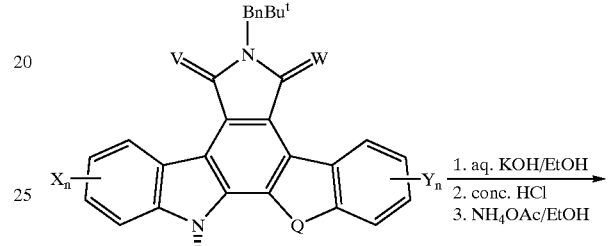
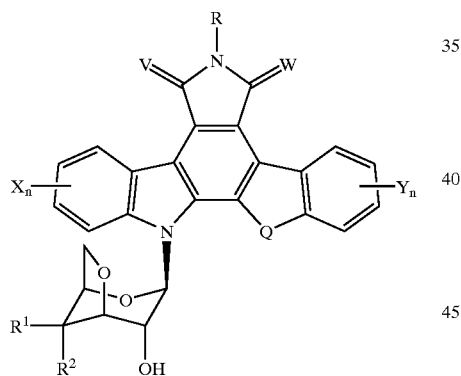
Example 3:
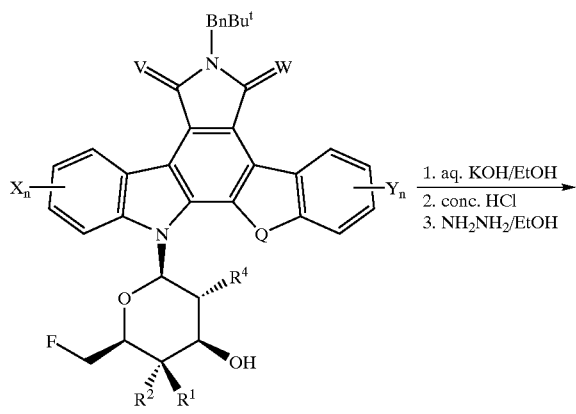
Scheme II:
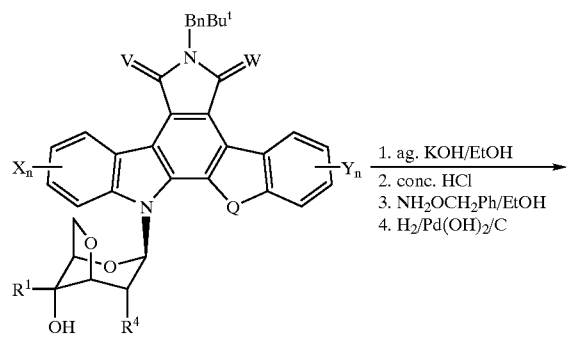

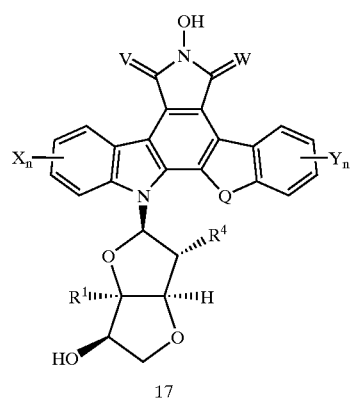
17
Scheme III
Example 1:
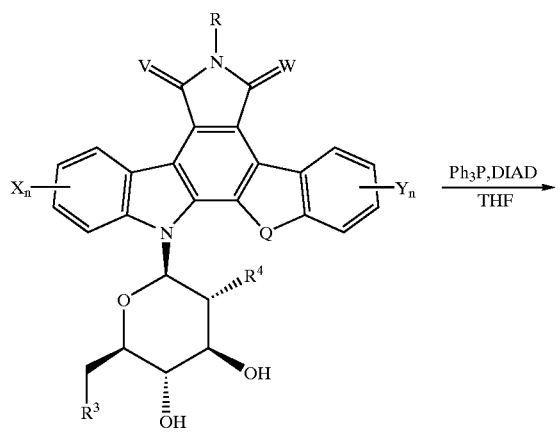
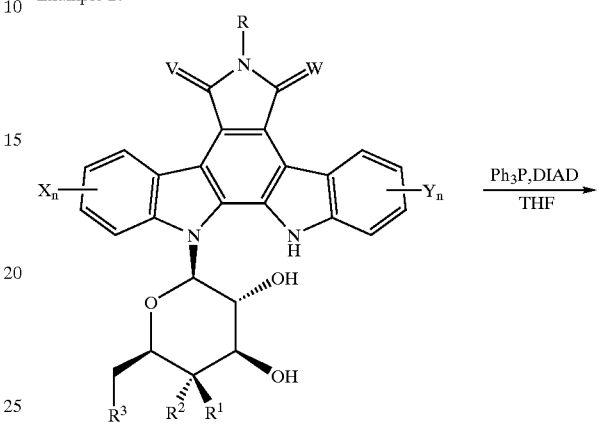
Example 2:
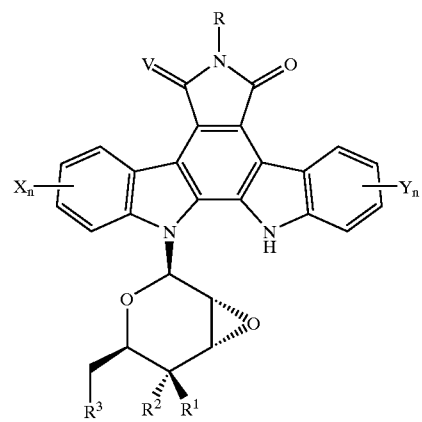
18
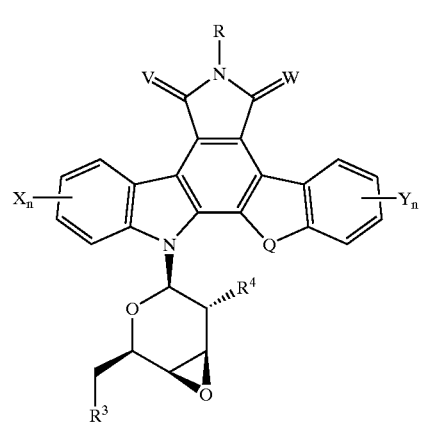
19

Scheme IV

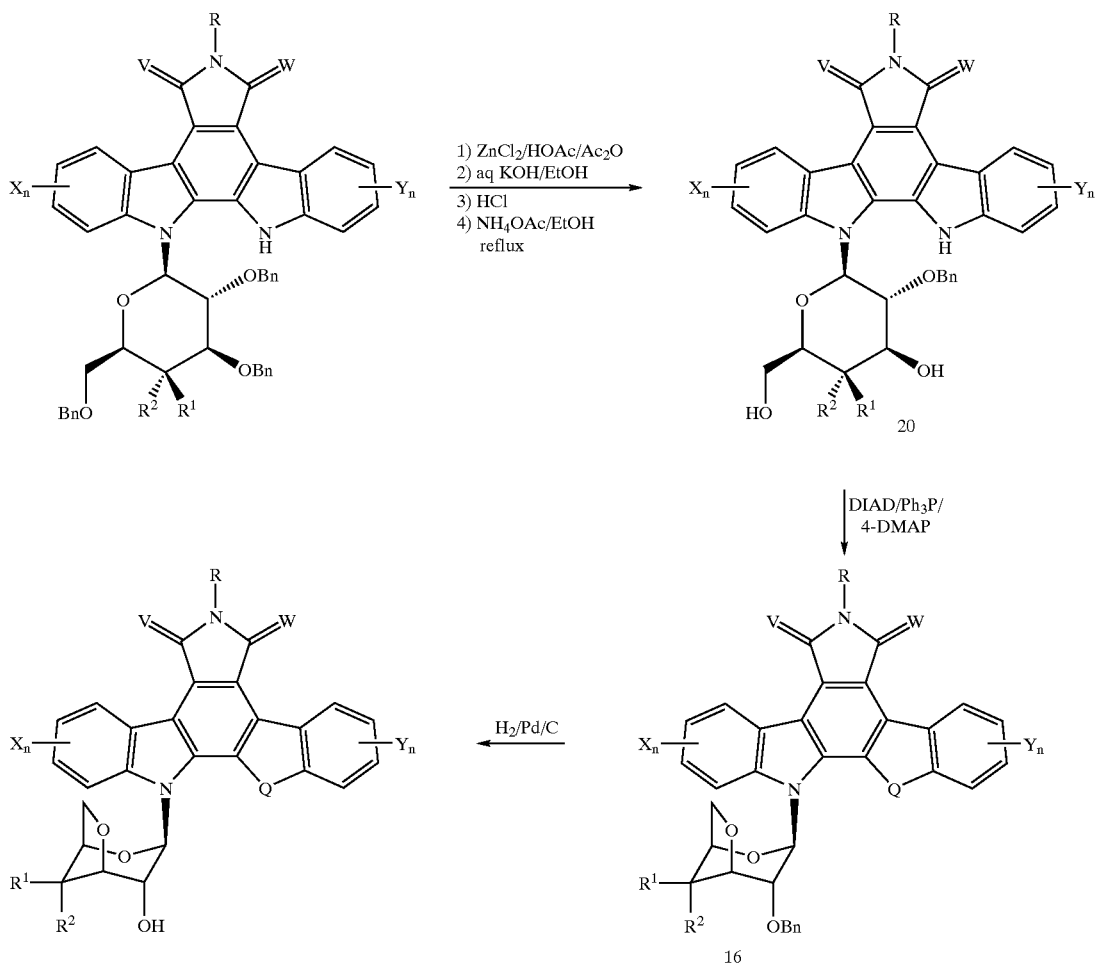

Compounds of the present invention and their methods of preparation are further described by the following non-limiting examples.

Synthesis of Intermediates

Several intermediate compounds as well as other conventional starting materials, used in the preparation of final products of compounds of the present invention, were generally known in the literature (WO 9807433) or were commercially available. Representative syntheses of some of these compounds are nevertheless provided hereinbelow.

The variables described in the above schemes have the same values as described in Formula (I), except for V in the above schemes which equals O, and W in the above schemes which equals $R^7$ and $R^8$ according to Formula (I). The benzyl (Bn) protecting group is illustrated as a particular moiety to "protect" a hydroxyl functionality, but other suitable protecting groups well known to one skilled in the art may be used in lieu of benzyl or the like. Such suitable protecting groups are adequately described in Green's *Protecting Groups in Organic Synthesis* (John Wiley and Sons, New York).

The starting materials in Scheme I, III and IV are glycosylated indolopyrrolocarbazoles and their preparation is described in WO9807433. Selective derivatization at the 6'-position may be achieved directly from compound of Formula 15 ($R^1$=H, $R^2$=OH), wherein all sugar hydroxyl groups are unprotected. Such chemoselective activation of the 6'-hydroxyl group to a good leaving group, such as mesylate or halide, is done in the presence of a base like triethylamine or pyridine using reagents for activation of a hydroxyl group to a good leaving group, such as methanesulfonyl chloride and others typically so used by one skilled in the art. More particular conditions are pyridine and methanesulfonyl chloride at 0° C.

Intramolecular nucleophilic displacement of the 6'-mesylate, or other such leaving groups, by the 3'-hydroxyl moiety is catalyzed by a base like triethylamine or Hunig's base, but more particularly fluoride ion (such as tetrabutylammonium fluoride). Typical solvents for this reaction are, but are not limited to, DMSO, NMP, THF, N,N-dimethylimidazolidinone or DMF at temperatures from 0° C. to 150° C., but more particularly at 85° C. The product of such an intramolecular displacement of a 6'-leaving group by the nucleophilic 3'-hydroxyl group is the 3',6'-anhydrosugar derivative of the indolopyrrolocarbazole of Formula (I).

Other methods for the synthesis of 3',6'-anhydrosugar analogs of Formula (I) from compounds of Formula 15 employ typical conditions of the Mitsunobu reaction, wherein the combination of triphenylphosphine (TPP) and diisopropylazodicarboxylate (DIAD) is used to activate the 6'-hydoxyl group towards intramolecular displacement by the 3'-hydroxyl group. Typical solvents for this reaction are, but not limited to, benzene, toluene, dioxane, more particularly THF or pyridine at temperatures from −15° C. to 80° C., and more particularly room temperature. Other reagents and/or combinations similar to TPP and DIAD may also be employed, such as diethylazodicarboxylate (DEAD) and TPP, or tri(O)-tolylphosphine, as well as TMAD and tributylphosphine and ADDP and trimethylphosphine, as well as combinations thereof Additives such as 4-dimethylaminopyridine (4-DMAP) and imidazole may also be used to improve the yield and accelerate the rate of this reaction. For example, more particular is the use of 4-dimethylaminopyridine (4-DMAP) in combination with TPP and DIAD in such solvents as THF or the like. The use of the additive 4-DMAP is preferred and a preferred substrate for this modification is the glycosylated indolopyrrollocarbozole of Formula 20 wherin $R^1=R^2=H$ and the hydroxyl moiety at the 2' position is preferably protected as the benzyl ether. In such a substrate, the 6'-hydroxyl moiety is activated towards intramolecular nucleophilic displacement by the free 3'-hydroxyl moiety, which is the only other hydroxyl moiety present.

Another method for the synthesis of 3',6'-anhydrosugar analogs of Formula (I) employs as a substrate the 6'-fluoro sugar analog of Formulas 16A or 16B. Under appropriate conditions, hydrazine or ammonium acetate in ethanol at reflux, the 6'-fluorine can serve as a leaving group towards the intramolecular nucleophilic displacement by the 3'-hydroxyl moiety giving products of Formula (I). These examples, wherein fluorine serves a leaving group, would not generally be expected by one skilled in the art.

Rearrangement of the 3',6'-anhydrosugar moiety under condiditons such as those typically used to convert the imide nitrogen to its free NH form (from its protected precursor) or to its N—O-benzyl form (from the same) can also serve to induce a novel rearrangement to yield glycosylated analogs such as the bicyclo [3.3.0] analog shown in Formula 17. Ethanol can be used as the solvent and at a reaction temperature including, but not limited to, that achieved by reflux of the solvent.

The synthesis of 3',4' and 2',3' anhydrosugar analogs of Formulas 18–19 proceed from their corresponding 3',4' and 2',3' trans-diol sugar analogs. Methods for the synthesis of compounds of Formulas 18–19 via dehydration utilize similar conditions employed for the synthesis of the 3',6'-anhydrosugar analogs of Formula (I) (vide supra). A particular method for the synthesis of compounds of Formulas 18 and 19 is the Mitsunobu reaction using TPP and DIAD in THF, although other reagent combinations and solvents delineated above for the synthesis of compounds of Formula (I) may also be employed. A particular temperature for the synthesis of 3',4' and 2',3'-anhydrosugar analogs of 18–19 is room temperature to 50° C.

All anhydrous reactions were performed under an atmosphere of nitrogen or argon using either commercially available dry solvents or freshly distilled solvents. Melting points were determined in an open capillary tube with a Thomas-Hoover melting point apparatus and are uncorrected. Column chromatography was performed using EM Science silica gel 60 (230–400 mesh) with the designated solvent system as eluant. Thin-layer chromatography was done on E. Merck silica gel 60 $F_{254}$ plates (0.5 mm). HPLC purity determinations were done using either a Shimadzu LC-10AS with a SPD-10AV UV-V is detector and one of the folowing columns; YMC Combiscreen ODS-A (4.6×50 mm), or HP Zorbax SB-C18 (4.6×750 mm); or, an HP 1090 DR5 with a diode array detector and a Waters Nova-Pak C18 column (3.9×150 mm). Infrared spectra were recorded on a Nicolet Protégé 460 FTIR as thin films or KBr pellets. $^1$HNMR spectra were recorded on either a Bruker AMX-400 or a Bruker ARX-500 NMR spectrometer and chemical shifts are expressed in parts per million (ppm or δ) with the solvent in use as internal standard. Coupling constants are given in hertz (Hz) and multiplets are designated as follows; singlet (s), doublet (d), triplet (t), quartet (q), muliplet (m), and broad (br). Low resolution mass spectra were determined on a Finnigan Matt TSQ-7000 triple stage quadrapole spectrometer (positive/negative ESI) operated in the negative ion mode.

Starting materials in the examples below may be synthesized by the methods disclosed in WO9807433, examples 1–106.

EXAMPLE 1

3,9-Difluoro-12,13-dihydro-13-[(3,6-anhydro)-β-D-glucopyranosyl]-5H-indolo[2,3-a]pyrrolo[3,4-c]carbazole-5,7(6H)-dione

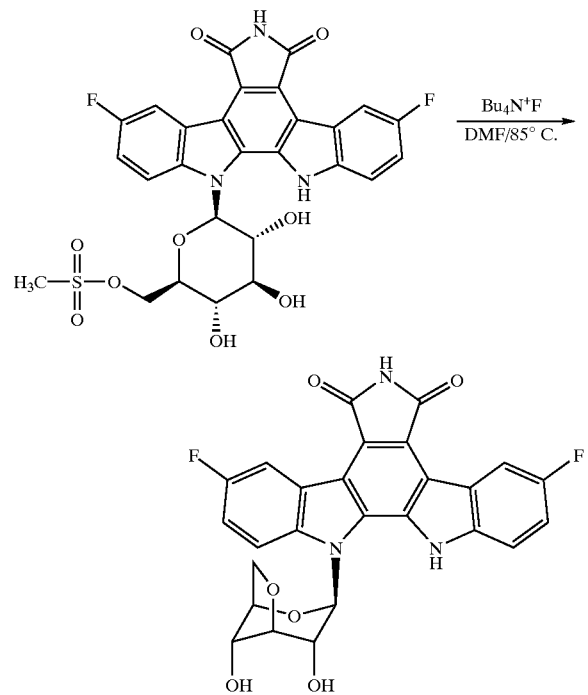

To a mixture of 3,9-difluoro-12,13-dihydro-13-[6-O-(methylsulfonyl)-β-D-glucopyranosyl]-5H-indolo[2,3-a]pyrrolo[3,4-c]carbazole-5,7(6H)-dione (8.0 mg, 0.013 mmol) and tetrabutylammonium fluoride trihydrate (30 mg, 0.095 mmol) was added anhydrous DMF (1 mL). The resulting solution was treated with activated powdered 4 A sieves, magnetically stirred under $N_2$ at room temperature for 45 min, and then heated at 85° C. for 18 h. The reaction mixture was diluted with EtOAc (300 mL), washed with water (4×75 mL) and brine (75 mL), and dried ($Na_2SO_4$). Evaporation in vacuo, followed by purification by flash chromatography on silica gel with 2–3% methanol in methylene chloride gave 4.8 mg (69%) of the pure title compound: 500 MHz COSY $^1$H NMR ($d_6$-DMSO) δ 8.86 (d, 1H, J=9.6, 2.7 Hz), 8.75 (dd, 1H, J=9.7, 2.6 Hz), 7.76 (dd, 1H, J=9.1, 4.4 Hz), 7.72 (dd, 1H, J=8.9, 4.5 Hz), 7.48 (ddd, 1H, J=9.1, 9.0, 2.7 Hz), 7.44 (ddd, 1H, J=9.0, 8.9, 2.8 Hz), 7.00 (d, 1H, J=7.7 Hz, 1'H), 4.58–4.55 (m, 2H, 3',6'H), 4.45 (d, 1H, J=7.7 Hz, 2'H), 4.16 (d, 1H, J=5.2 Hz, 6"H), 4.10 (d, 1H, J=9.9 Hz, 5'H), 4.01–3.99 (d, 1H, 4'H); FAB mass spectrum, m/e 506 (M+).

EXAMPLE 2

3,9-Difluoro-12,13-dihydro-13-[(3,6-anhydro)-α-D-glucopyranosyl]-5H-indolo[2,3-a]pyrrolo[3,4-c]carbazole-5,7(6H)-dione

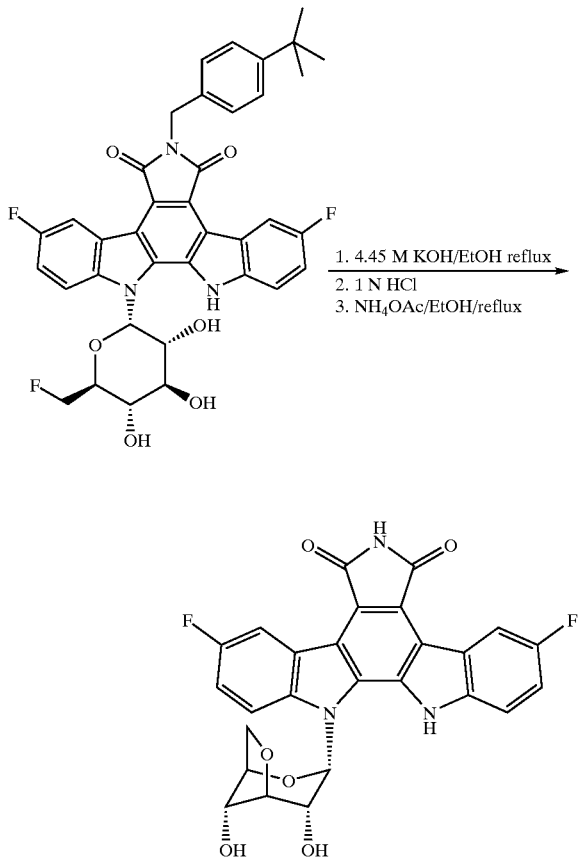

To a stirred solution of 3,9-Difluoro-12,13-dihydro-13-[(6-fluoro)-α-D-glucopyranosyl]-5H-indolo[2,3-a]pyrrolo[3,4-c]carbazole-5,7(6-N-[4-(t-butyl)benzyl]-)-dione in absolute ethanol (150 mL) was added 4.45 M KOH (55 mL). The resulting blood red solution was heated to reflux until all the ethanol was boiled off and a red solid gummed out. The reaction was cooled to room temperature, treated with 1 N HCl (25 mL), and solid ammonium acetate (100 g) was added. The resulting suspension was heated to reflux for 18 h and the volume was concentrated by about two thirds. The resulting suspension was partioned with ethyl acetate and concentrated HCl. The orgainc layer was washed with water, sodium bicarbonate, and brine, and dried (Na$_2$SO$_4$). Evaporation in vacuo followed by flash column chromatography on silica gel using an acetone/methylene chloride gradient gave the title compound: 500 MHz COSY $^1$H NMR (d$_6$-DMSO) δ 8.86 (d, 1H, J=9.6, 2.7 Hz), 8.75 (dd, 1H, J=9.7, 2.6 Hz), 7.76 (dd, 1H, J=9.1, 4.4 Hz), 7.72 (dd, 1H, J=8.9, 4.5 Hz), 7.48 (ddd, 1H, J=9.1, 9.0, 2.7 Hz), 7.44 (ddd, 1H, J=9.0, 8.9, 2.8 Hz), 7.00 (d, 1H, J=7.7 Hz, 1'H), 4.58–4.55 (m, 2H, 3',6'H), 4.45 (d, 1H, J=7.7 Hz, 2'H), 4.16 (d, 1H, J=5.2 Hz, 6"H), 4.10 (d, 1H, J=9.9 Hz, 5'H), 4.01–3.99 (d, 1H, 4'H); ESI (NEG) mass spectrum, m/e 504 (M−H)−.

EXAMPLE 3

3,9-Difluoro-12,13-dihydro-13-[(3,6-anhydro)-β-D-glucopyranosyl]-5H-indolo[2,3-a]pyrrolo[3,4-c]carbazole-5,7(6-N-hydroxyl)-dione

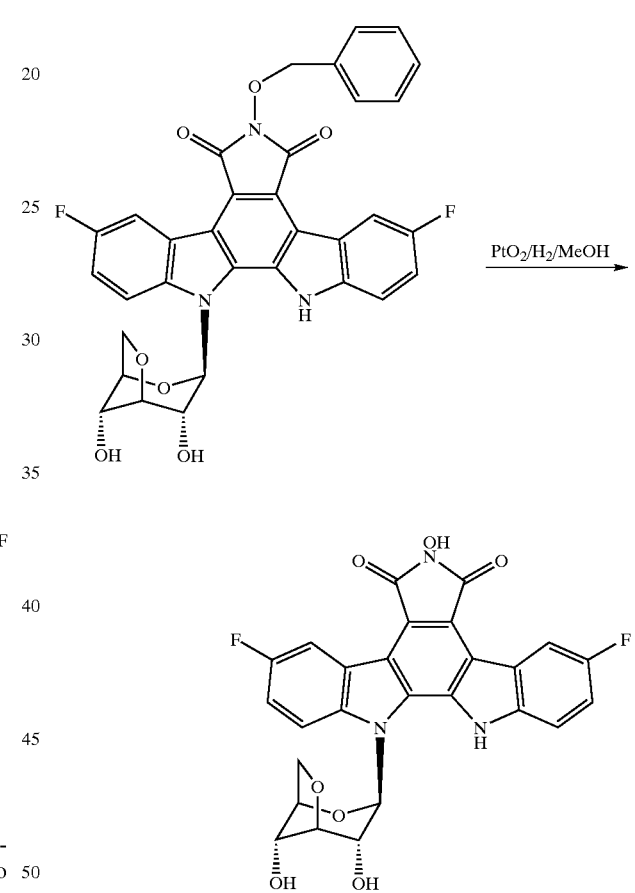

To a solution of 3,9-Difluoro-12,13-dihydro-13-[(3,6-anhydro)-β-D-glucopyranosyl]-5H-indolo[2,3-a]pyrrolo[3,4-c]carbazole-5,7(6-N—O-benzyl)-dione: (10 mg) in methanol was added platinum (IV) oxide. The resulting suspension was treated with hydrogen at 70 PSI on a Parr shaker for 18 h. The catalyst was filtered thru a small pad of celite and the solvent removed in vacuo. Purification on Sephadex LH-20 with methanol elution gave 7.1 mg of the title compound: 300 MHz $^1$H NMR (d$_6$-Acetone) δ 8.90–8.70 (m, 2H), 7.95–7.20 (m, 4H), 6.62 (d, 1H, J=7.5 Hz), 5.20–4.05 (m, 6H); ESI (NEG) mass spectrum, m/e 520 (M−H)−.

EXAMPLE 4

3,9-Difluoro-12,13-dihydro-13-[(3,6-anhydro)-β-D-glucopyranosyl]-5H-indolo[2,3-a]pyrrolo[3,4-c]carbazole-5,7(6-N-amino)-dione

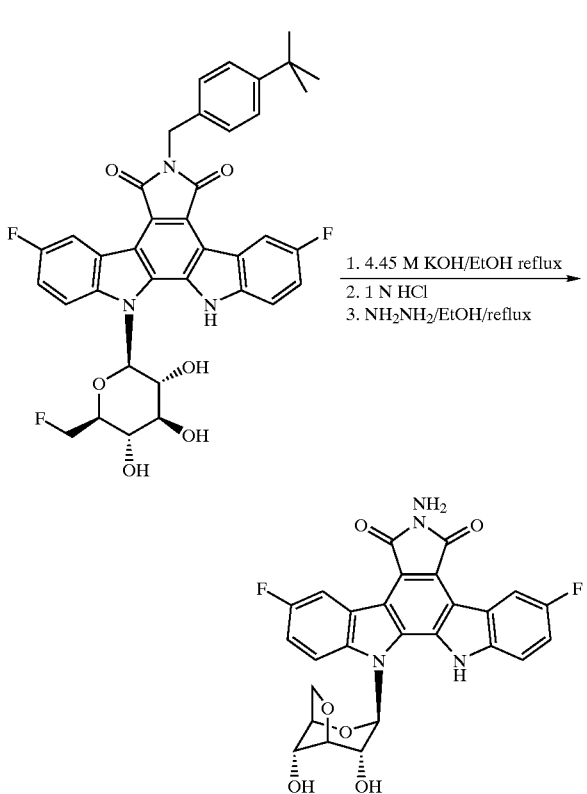

To a stirred solution of 3,9-Difluoro-12,13-dihydro-13-[(6-fluoro)-β-D-glucopyranosyl]-5H-indolo[2,3-a]pyrrolo[3,4-c]carbazole-5,7(6-N-[4-(t-butyl)benzyl]-)-dione (150 mg) in absolute ethanol (250 mL) was added 4.45 M KOH (50 mL). The resulting blood red solution was heated to reflux until all of the ethanol boiled off and a red solid gummed out. The reaction was cooled to room temperature and treated with conc. HCl (51 mL). Hydrazine (75 g) and additional ethanol (250 mL) were added and the reaction was allowed to reflux for 5 days. The reaction volume was concentrated by approximately ⅔ volume, cooled to room temperature, and partitioned with ethyl acetate and water. The orgainc layer was washed with water, sodium bicarbonate, and brine, and dried ($Na_2SO_4$). Rotary evaporation followed by purification on Sephadex LH-20 chromatography in methanol gave the title compound: 500 MHz COSY $^1$H NMR ($d_6$-DMSO) δ 8.90 (dd, 1H), 8.79 (dd, 1H), 8.05 (dd, 1H), 7.81 (dd, 1H), 7.53–7.43 (m, 2H), 6.69 (d, 1H, J=7.9 Hz, 1'H), 5.01 (s, OH), 5.01–4.93 (dd, 1H, 4'H), 4.60 (brs, 1H, 5'H), 4.50 (brs, 1H, 3'H), 4.17 (brs, 1H, 2'H), 3.99–3.95 (m, 2H, 6'H, 6"H); FAB mass spectrum, m/e 520 ($M^+$).

EXAMPLE 5

3,9-Difluoro-12,13-dihydro-13-[(2,6-dihydroxy)-(4,8-dioxa)-bicyclo[3.3.0]oct-3-yl]-5H-indolo[2,3-a]pyrrolo[3,4-c]carbazole-5,7(6-N—O-benzyl)-dione

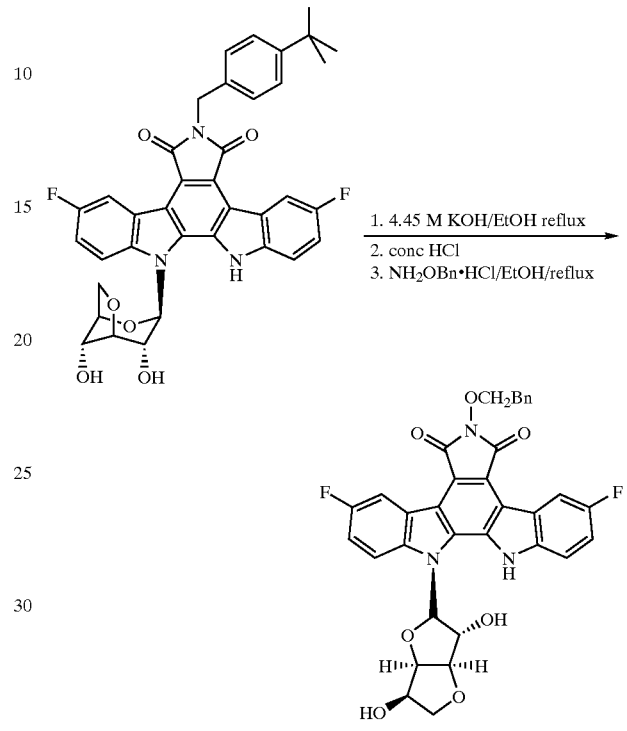

To a stirred solution of 3,9-Difluoro-12,13-dihydro-13-[(3,6-anhydro)-β-D-glucopyranosyl]-5H-indolo[2,3-a]pyrrolo[3,4-c]carbazole-5,7(6-N-[4-(t-butyl)benzyl]-)-dione: (22.5 mg) in absolute ethanol (28 mL) was added 4.45 M KOH (7 mL). The resulting blood red solution was heated to reflux until all of the ethanol boiled off and a red solid gummed out. The reaction was cooled to room temperature and treated with conc. HCl (3 mL). O-benzylhydroxylamine hydrochloride (10 g) and additional ethanol (20 mL) were added and the reaction was allowed to reflux overnight. The reaction volume was concentrated by approximately ½ volume, cooled to room temperature, and partitioned with ethyl acetate and water. The organic layer was washed with water, and brine, and dried ($Na_2SO_4$). Rotary evaporation followed by purification by flash chromatography on silica gel using a methylene chloride/ethyl acetate gradient gave 8.7 mg of the title compound as an orange solid: 500 MHz COSY $^1$H NMR ($d_6$-DMSO) δ 8.81 (dd, 1H, J=2.6, 9.5 Hz, H-8), 8.72 (dd, 1H, J=2.6, 9.7 Hz, H-4), 8.06 (dd, 1H, J=4.3, 9.3 Hz, H-11), 7.82 (dd, 1H, J=4.6, 9.0 Hz, H-1), 7.64–7.35 (m, 7H), 6.72 (d, 1H, J=4.0 Hz, 5'OH), 6.65 (d, 1H, J=8.0 Hz, 1'H), 5.67 (d, 1H, J=5.6 Hz, 2'OH), 5.32 (s, 2H, O—$CH_2$-Ph), 4.98 (t, 1H, $J_{3',4'}$=6.2 Hz, $J_{4',5'}$=6.2 Hz, 4'H), 4.62 (ddd 1H, $J_{4',5'}$=6.2 Hz, $J_{5',6'}$=4.6 Hz, $J_{5',OH}$=4.0 Hz, 5'H), 4.50 (dd, 1H, $J_{2',3'}$=3.8 Hz, $J_{3',4'}$=6.2Hz, 3'H), 4.13 (ddd, 1H, $J_{1',2'}$=8.0 Hz, $J_{2',3'}$=3.8 Hz, $J_{2',OH}$=5.6 Hz, 2'H), 3.98 (d, 2H, $J_{5',6'}$=4.6 Hz, $J_{5',6''}$=0 Hz, 6'H, 6"H); FAB mass spectrum, m/e 611 ($M^+$); ESI (NEG) mass spectrum, m/e 610 $(M-H)^-$.

EXAMPLE 6

3,9-Difluoro-12,13-dihydro-13-[(2,6-dihydroxy)-(4,8-dioxa)-bicyclo[3.3.0]oct-3-yl]-5H-indolo[2,3-a]pyrrolo[3,4-c]carbazole-5,7(6-N-hydroxyl)-dione

EXAMPLE 7

3,9-Difluoro-12,13-dihydro-13-[(2,3-anhydro)-(4,6-difluoro)-β-D-glucopyranosyl]-5H-indolo[2,3-a]pyrrolo[3,4-c]carbazole-5,7(6H)-dione

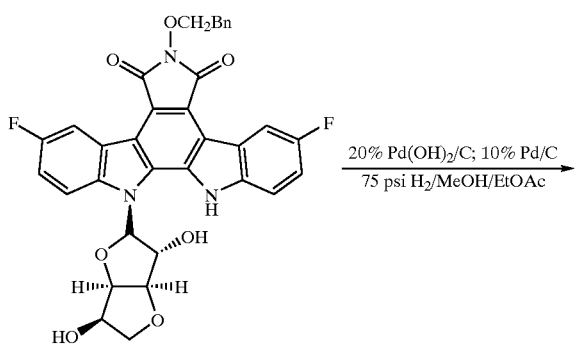

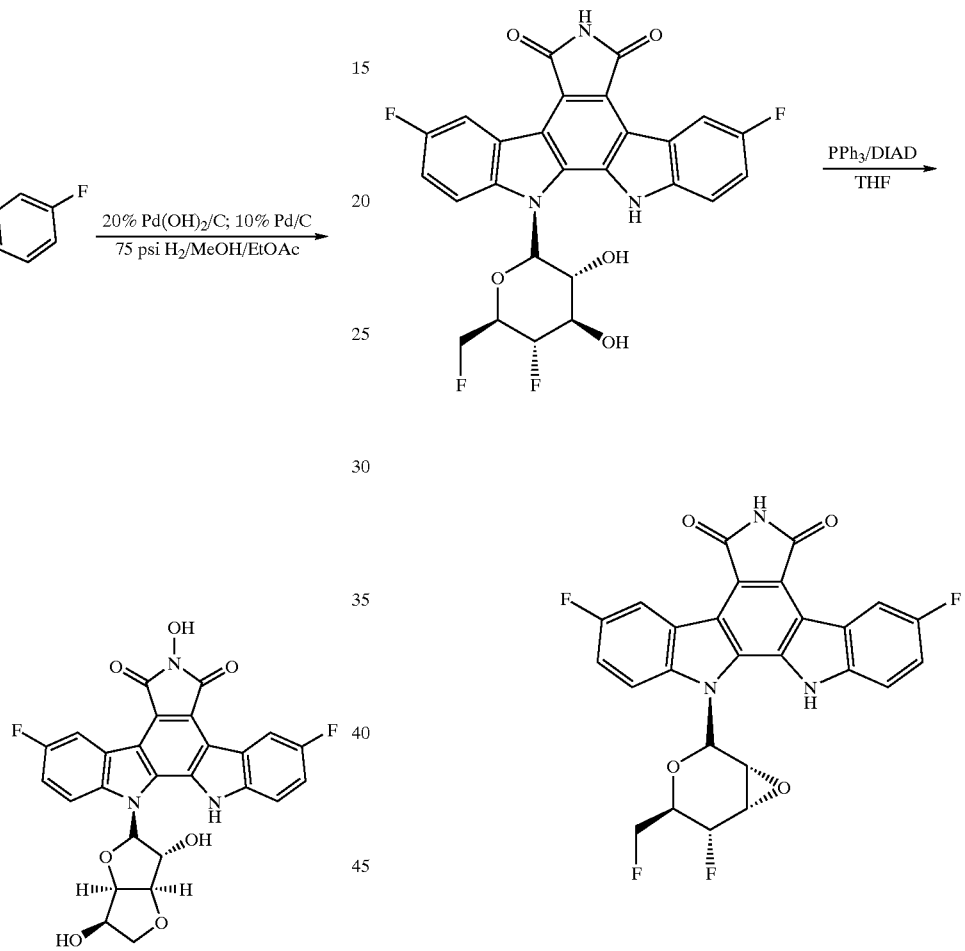

To a solution of the product from Example 5 (6.4 mg) in 1:1 methanol: ethyl acetate (3.5 mL) was added 20% palladium hydroxide/C and 10% palladium/C. The resulting suspension was treated with hydrogen at 75 PSI on a Parr shaker for 18 h. The catalyst was filtered thru a small pad of celite and the solvent removed in vacuo. Purification on Sephadex LH-20 with methanol elution gave 3.6 mg of the title compound: 500 MHz COSY $^1$H NMR ($d_6$-DMSO) δ 8.77 (dd, 1H), 8.59 (dd, 1H), 7.99 (dd, 1H), 7.72 (dd, 1H), 7.45–7.25 (m, 2H), 6.87 (brs, 1H), 4.49–4.84 (m, 1H,), 4.58–4.43 (m, 2H), 4.34 (brs, 1H), 4.08–3.88 (m, 2H); FAB mass spectrum, m/e 521 (M$^+$).

To a stirred solution of 3,9-Difluoro-12,13-dihydro-13-[(4,6-difluoro)-β-D-glucopyranosyl]-5H-indolo[2,3-a]pyrrolo[3,4-c]carbazole-5,7(6H)-dione (23.7 mg, 0.045 mmol) and triphenylphosphine (36.6 mg, 0.140 mmol) in anhydrous THF (1.0 mL) was added diisoproply azodicarboxylate (27 μL, 0.137 mmol). The reaxtion was allowed to stir at room temperature for 1 h, then warmed to 50° C. for 3 h. Additional triphenylphosphine (39 mg, 0.149 mmol) and diisoproply azodicarboxylate (29 μL, 0.148 mmol) were added and the resulting red solution was stirred at 50° C. overnight. The reaction was quenched with water (1 drop) and the solvent removed in vacuo. Purification on Sephadex LH-20 gave 2.0 mg of the title compound: 500 MHz COSY $^1$H NMR ($d_6$-DMSO) δ 8.88 (dd, 4H), 8.77 (dd, 1H), 8.16–8.05 (m, 1H), 7.81–7.69 (m, 1H), 7.43 (brs, 1H, 1'H), 5.11 (dd, 2H, 4'H, 4"H), 4.76 (s, 1H, 6"H), 4.67 (s, 1H, 6'H), 4.52–4.36 (m, 1H, 5'H), 4.06–3.91 (m, 2H, 3'H, 2'H); ESI (NEG) mass spectrum, m/e 508 (M–H)⁻.

EXAMPLE 8

3,9-Difluoro-12,13-dihydro-13-[(3,4-anhydro)-β-D-glucopyranosyl]-5H-indolo[2,3-a]pyrrolo[3,4-c]carbazole-5,7(6H)-dione

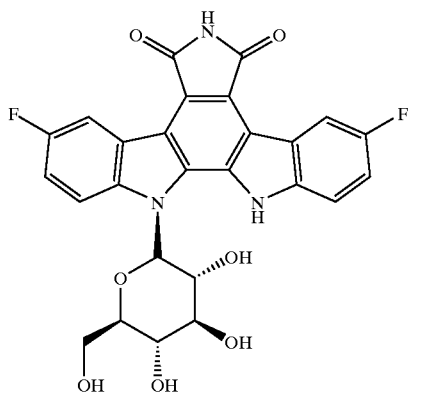

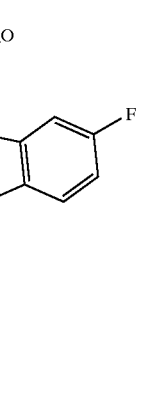

To a stirred solution of 3,9-Difluoro-12,13-dihydro-13-[β-D-glucopyranosyl]-5H-indolo[2,3-a]pyrrolo[3,4-c]carbazole-5,7(6H)-dione (240 mg, 0.495 mmol) and triphenylphosphine (263 mg, 1.00 mmol) in anhydrous THF (10 mL) was added diisoproply azodicarboxylate (200 μL, 1.01 mmol). The resulting red solution was allowed to stir at room temperature for 2 h, after which is was quenched with water (5 drops) and evaporated to dryness in vacuo. Flash column chromatography on silica gel using an acetone: hexane gradient followed by Sephadex LH-20 purification in methanol gave 43.4 mg (23%) of the title compound: 500 MHz COSY ¹H NMR (d₆-DMSO) δ 11.22 (brs, 1H), 8.85 (dd, 1H), 8.76 (dd, 1H), 7.97 (brs, 1H), 7.65 (brs, 1H), 7.58–7.39 (m, 2H), 6.21 (d, 1H, 1'H), 5.88 (d, 1H, 2'OH), 5.40 (brs, 1H, 6'OH), 4.71 (brs, 1H, 5'H), 4.12 (brs, 1H, 2'H), 4.01–3.82 (m, 2H, 6'H, 6"H), 3.74 (brs, 1H, 4'H), 3.44 (d, 1H, 3'H); ESI (NEG) mass spectrum, m/e 504 (M–H)⁻.

EXAMPLE 9

3,9-Difluoro-12,13-dihydro-13-[(2-O-benzyl)-(4-dexoy)-β-D-glucopyranosyl]-5H-indolo[2,3-a]pyrrolo[3,4-c]carbazole-5,7(6H)-dione

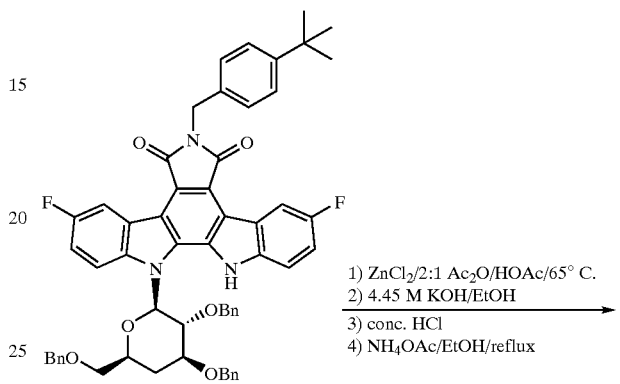

A solution of zinc chloride (6.5 g, 47.7 mmol) in 2:1 acetic anhydride/acetic acid (48 mL) was added to a suspension of 3,9-Difluoro-12,13-dihydro-13-[2,3,6-(O-benzyl)-(4-deoxy)-β-D-glucopyranosyl]-5H-indolo[2,3-a]pyrrolo[3,4-c]carbazole-5,7(6-N-[4-(t-butyl)benzyl]-)-dione (5.0 g, 5.41 mmol) in 2:1 acetic anhydride/acetic acid (120 mL). The reaction mixture was heated to 65° C. for 22 h, cooled to room temperature, and diluted with ethyl acetate. The organic layer was washed with water (3×200 mL), sodium bicarbonate (3×200 mL), water (2×200 mL), and brine (2×200 mL), and dried (Na₂SO₄). Evaporation in vacuo gave a crude product which was deblocked according to the procedure described in WO9807433 to give 1.38 g (43%) of the title compound: 300 MHz ¹H NMR (d₆-DMSO) δ 11.75 (brs, 1H), 11.25 (brs, 1H), 8.85 (dd, 1H, J=9.6, 3.1 Hz), 8.77 (dd, 1H, J=9.8, 2.8 Hz), 8.00 (dd, 1H, J=9.6, 4.4 Hz), 7.70 (dd, 1H, J=8.8, 4.6 Hz), 7.53–7.43 (m, 2H), 6.90 (t, 1H, J=7.7 Hz), 6.77 (dd, 2H, 7.7, 7.1 Hz), 6.37 (d, 1H, 9.1 Hz), 6.14 (t, 1H), 6.08 (d, 2H, J=7.1 Hz), 5.28 (d, 1H, 5.8 Hz), 4.18–3.64 (m, 5H), 3.21–3.17 (m, 2H), 2.42–2.28 (m, 1H), 2.07–1.98 (m, 1H); ESI (NEG) mass spectrum, m/e 596 (M–H)⁻.

EXAMPLE 10

3,9-Difluoro-12,13-dihydro-13-[(3,6-anhydro)-(2-O-benzyl)-(4-deoxy)-β-D-glucopyranosyl]-5H-indolo[2,3-a]pyrrolo[3,4-c]carbazole-5,7(6H)-dione

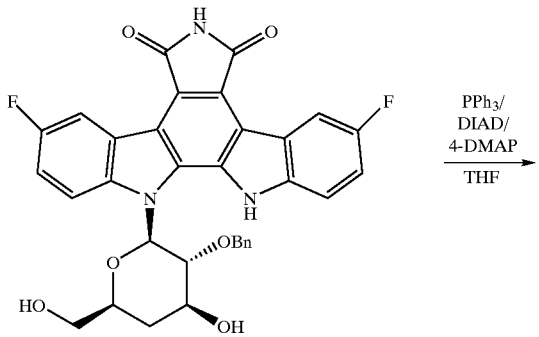

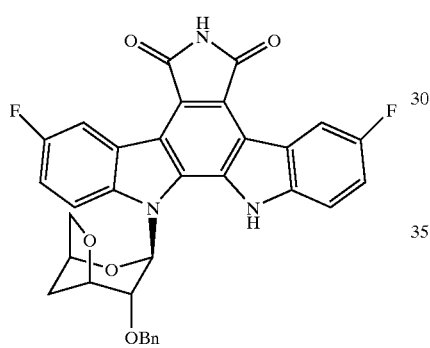

EXAMPLE 11

3,9-Difluoro-12,13-dihydro-13-[(3,6-anhydro-4-deoxy)-β-D-glucopyranosyl]-5H-indolo[2,3-a]pyrrolo[3,4-c]carbazole-5,7(6H)-dione

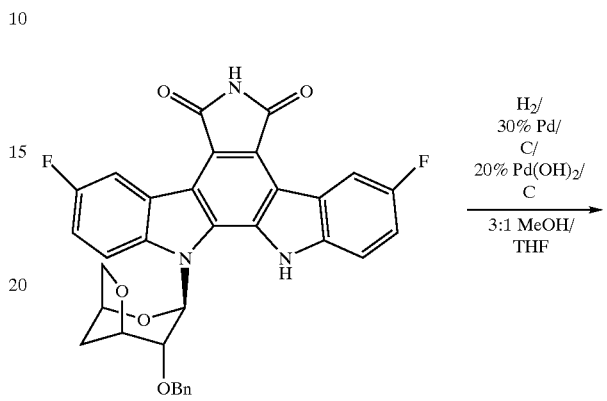

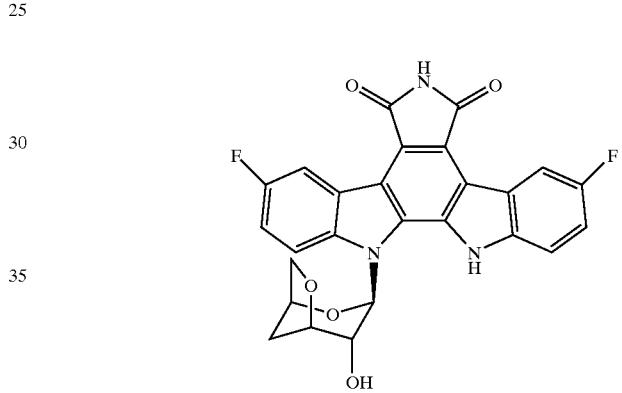

To a 5–10° C. solution of the product from Example 9 (1.03 g, 1.72 mmol), triphenyl phosphine (1.82 g, 6.93 mmol) and 4-dimethylaminopyridine (539 mg, 4.41 mmol) in anhydrous THF (95 mL) was added diisopropyl azodicarboxylate (1.37 mL, 6.96 mmol). The resulting red solution was stirred at room temperature for 90 minutes, cooled to 0° C., quenched with water (3.5 mL) and the solvent removed in vacuo. The resulting residue was evaporated from absolute ethanol (100 mL), redissolved in a mixture of THF and methylene chloride and applied to a flash column packed in methylene chloride. The column was eluted with a gradient from methylene chloride to 5% ethyl acetate in methylene chloride to give 693 mg (69%) of the title compound: 500 MHz COSY $^1$H NMR (d$_6$-DMSO) δ 12.0 (brs, 1H), 11.27 (s, 1H), 8.92–8.84 (m, 2H), 7.84–7.72 (m, 2H), 7.55–7.50 (ddd, 1H), 7.45–7.37 (ddd, 1H), 6.86 (t, 1H), 6.62 (t, 2H), 6.44 (d, 1H, J=7.35 Hz, 1'H), 6.34 (d, 2H), 5.00 (brs, 1H, 5'H), 4.65 (d, 1H, J=5.7 Hz, 3'H), 4.33 (d, 1H, J=12.4 Hz, 2'-CH$_2$Ph), 4.21 (d, 1H, J=9.2 Hz, 6'H), 4.10–4.00 (m, 2H, 2'H and 2'-CH$_2$Ph), 3.81 (d, 1H, J=9.2 Hz, 6"H), 3.35–3.25 (m, 1H, 4'H), 2.08–1.99 (m, 1H, 4"H); ESI (NEG) mass spectrum, m/e 578 (M−H)$^-$.

To a solution of the product from Example 10, (733 mg, 1.26 mmol) in 3:1 methanol/THF (400 mL) was added 30% palladium on carbon (510 mg) and 20% palladium hydroxide on carbon (1.25 g). The resulting suspension was flushed with nitrogen, then with hydrogen and allowed to stir overnight under a hydrogen atmosphere. The reaction was filtered thru a small pad of Celite, the catalyst washed with THF and methanol, and the filtrate evaporated in vacuo. The resulting residue was evaporated onto silica gel, applied to a flash column packed in 10% acetone/methylene chloride, and the column was eluted with a gradient from 10% acetone/methylene chloride to 80% acetone/methylene chloride. Further purification on Sephadex LH-20 in acetone gave 299 mg (49%) of the title compound: 500 MHz COSY $^1$H NMR (d$_6$-DMSO) δ 11.99 (brs, 1H), 11.26 (s, 1H), 9.00–8.96 (dd, 1H), 8.90–8.85 (dd, 1H), 7.95–7.82 (m, 2H), 7.62–7.47 (m, 2H), 6.33 (d, 1H, J=7.20 Hz, 1'H), 5.76 (d, 1H, J=5.10 Hz, 2'OH), 4.99 (brs, 1H, 5'H), 4.40 (d, 1H, J=5.80, 3'H), 4.36–4.32 (m, 1H, 2'H), 4.22 (d, 1H, J=8.9 Hz, 6'H), 3.83 (d, 1H, J=8.9 Hz, 6"H), 3.27 (d, 1H, J=9.65 Hz, 4'H), 2.06–1.99 (m, 1H, 4"H); ESI (NEG) mass spectrum, m/e 488 (M−H)$^-$.

EXAMPLE 12

2,10-Difluoro-12,13-dihydro-12-[(3,4-anhydro)-β-D-glucopyranosyl]-5H-indolo[2,3-a]pyrrolo[3,4-c]carbazole-5,7(6H-dione

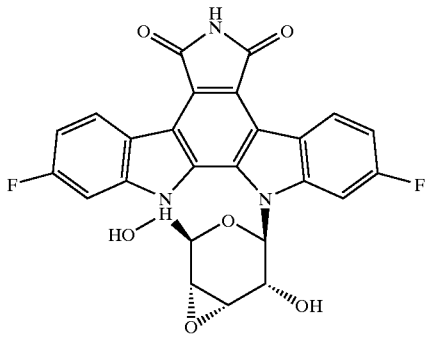

Diisopropyl azodicarboxylate (64 μL, 0.32 mmol) was added dropwise to a cold (0° C.) solution of 2,10-difluoro-12,13-dihydro-12-[β-D-glucopyranosyl]-5H-indolo[2,3-a]pyrrolo[3,4-c]carbazole-5,7(6H)-dione (0.15 g, 0.29 mmol) and triphenylphosphine (83 mg, 0.32 mmol) under nitrogen. The mixture was allowed to gradually warm up to room temperature, stirred for 16 h, diluted with ethyl acetate and washed with saturated sodium bicarbonate solution and brine. Following drying and solvent concentration, the residue was purified by flash chromatography on silica gel (elution with 10% methanol in chloroform) to furnish 2,10-difluoro-12,13-dihydro-12,13-[1,6-anhydro-β-D-glucopyranosyl]-5H-indolo[2,3-a]pyrrolo[3,4-c]carbazole-5,7(6H)-dione (8.7 mg, 12%) as a yellow solid and the title compound (75.7 mg, 52%) also as a yellow solid, m.p. >300° C.; $^1$H NMR (500 MHz, DMSO-$d_6$) δ 11.28 (s, 1H), 11.20 (s, 1H), 9.12 (dd, J=8.5, 6.0 Hz, 1H), 9.04 (dd, J=7.2, 5.8 Hz, 1H), 7.83 (d, J=9.2 Hz, 1H), 7.37 (d, J=8.9 Hz, 1H), 7.29–7.21 (m, 2H), 6.18 (d, J=8.2 Hz, 1H), 5.90 (d, J=6.4 Hz, 1H), 5.48 (br s, 1H), 4.71–4.69 (m, 1H), 4.08 (m, 1H), 3.96 (m, 1H), 3.89–3.88 (m, 1H), 3.73 (s, 1H), 3.42 (d, J=3.8 Hz, 1H); IR (KBr, cm$^{-1}$) 3458, 3368, 2929, 1747, 1698, 1624, 1578, 1452, 1406, 1385, 1330, 1232, 1171, 1115, 1061, 919, 836, 762; MS (−ESI, M−H$^-$) m/z 504.

EXAMPLE 13

3,9-Difluoro-13-(3,6-anhydro-α-D-glucopyranosyl)-5H,13H-benzo[β]thienyl[2,3-a]pyrrolo[3,4-c]carbazole-5,7(6H)-dione

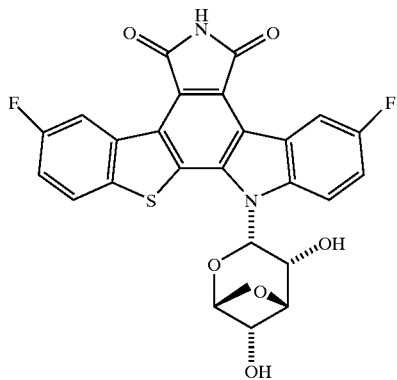

Diisopropyl azodicarboxylate (2.2 mL, 11.21 mmol) was added dropwise to a cold (0° C.) suspension of 3,9-difluoro-6-methyl-5H, 13H-benzo[β]thienyl[2,3-a]pyrrolo[3,4-c]carbazole-5,7-dione (2.0 g, 5.10 mmol), triphenylphosphine (2.94 g, 11.21 mmol)and 6-fluoro-2,3,4-tribenzyl-D-glucopyranose (3.46 g, 7.64 mmol) under nitrogen. The mixture was allowed to gradually warm up to room temperature where it stirred for 2 h before it was cooled to 0° C. and treated with additional 6-fluoro-2,3,4-tribenzyl-D-glucopyranose (1.73 g, 3.82 mmol), triphenylphosphine (1.47 g, 5.61 mmol) and DIAD (1.1 mL, 5.61 mmol). After stirring for an additional 1 h at room temperature, the mixture was diluted with ethyl acetate and washed with water and brine. Following drying and solvent concentration, the residue was purified by flash chromatography on silica gel (gradient elution with 10% ethyl acetate in hexane followed by 15% and finally with ethyl acetate/tetrahydrofuran/hexane (15/5/80) to furnish the coupled product as a yellow foam which was carried on directly. The substrate was taken up in 95% ethanol (50 mL) and subjected to transfer hydrogenation with 20% palladium hydroxide on carbon (1.5 g) and cyclohexene (40 mL). The mixture was refluxed for 7 h before additional catalyst (1.5 g), cyclohexene (40 mL) and ethanol (50 mL) were added. After an additional 16 h at reflux, the mixture was filtered hot through Celite was washed with THF and methanol. The filtrate was concentrated down in vacuo. Purification of the residue by flash chromatography on silica gel (elution with 10% methanol in chloroform) yielded the debenzylated product as a yellow solid which was taken on further. Potassium hydroxide (5M, 10 mL) was added to a stirred suspension of the debenzylated product in absolute ethanol (2 mL) at room temperature. The mixture was stirred at room temperature for 2d before it was heated to 50° C. and sparged with air in order to remove most of the ethanol. After cooling for 15 min at 0° C., concentrated hydrochloric acid was added in portions until a precipitate formed and remained (pH=1). This suspension was stirred at room temperature for 24 h before it was diluted with ethyl acetate and tetrahydrofuran and washed with 1N HCl, brine, dried and concentrated. Solid ammonium acetate (10 g, xs) was added to the residue and the mixture was fused at 120° C. was 2 h before it was cooled to room temperature, diluted with ethyl acetate and THF and washed with saturated sodium bicarbonate solution until a pH=9 was achieved. Solid sodium carbonate was initially used in order to quench most of the acetic acid. The organic layer was then separated, washed with brine, dried and concentrated. Purification of the residue by flash chromatography on silica gel (gradient elution with 10% methanol in chloroform followed by 15% and finally 20% methanol in chloroform) afforded a three component inseparable mixture which was further purified by LH-20 chromatography (methanol, 0.3 mL/min, 36 h) to furnish 3,9-difluoro-13-(6-fluoro-6-deoxy-β-D-glucopyranosyl)-5H, 13H-benzo[β]thienyl[2,3-a]pyrrolo[3,4-c]carbazole-5,7(6H-dione (226.1 mg, 8.2%, 4 steps), 3,9-difluoro-6-methyl-13-(6-fluoro-6-deoxy-β-D-glucopyranosyl)-5H,13H-benzo[β]thienyl[2,3-a]pyrrolo[3,4-c]carbazole-5,7(6H)-dione (20.1 mg, 0.7%, 4 steps), and the title compound (10.1 mg, 0.4%, 4 steps) as a yellow solid, m.p. >305° C.; $^1$H NMR (500 MHz, DMSO-$d_6$) δ 11.50 (v br s, 0.7H), 9.54 (d, J=11.4 Hz, 1H), 8.75 (dd, J=9.7, 2.5 Hz, 1 H), 8.46 (dd, J=9.2, 4.8 Hz, 1H), 8.11 (dd, J=8.7, 5.3 Hz, 1H), 7.40–7.32 (m, 2H), 7.00 (d, J=3.1, 1H), 4.63 (s, 1H), 4.42–4.39 (m, 2H), 4.31–4.29 (m, 1H), 4.31–4.29 (m, 1H), 4.20 (d, J=9.0 Hz, 1H), 4.11 (s, 1H), −0.08 (br s, 2H); IR (KBr, cm$^{-1}$) 3341, 3184, 2961, 1756, 1699, 1620, 1604, 1573, 1476, 1457, 1424, 1328, 1259, 1200, 1165, 1115, 1101, 1081, 1062, 1019, 920, 878, 810, 762; MS (−ESI, M−H$^-$) m/z 521, (+ESI, M+H$^+$) m/z 523.

EXAMPLE 14

12-(3,6-Anhydro-β-D-glucopyranosyl)-2,10-difluoro-12,13-dihydro-5H-indolo[2,3-a]pyrrolo[3,4-c]carbazole-5,7(6H)-dione:

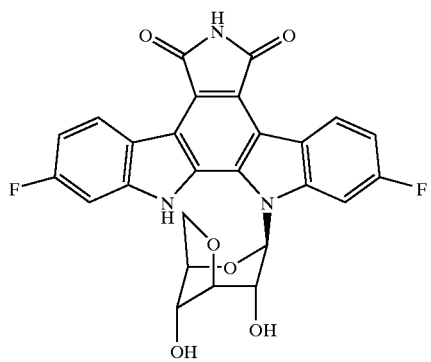

2,10-Difluoro-12,13-dihydro-12-[β-D-glucopyranosyl]-5H-indolo[2,3-a]pyrrolo[3,4-c]carbazole-5,7(6H)-dione (1.0 g, 1.91 mmol) was dissolved in dry pyridine under nitrogen at room temperature and treated with flame-dried, powdered 4A molecular sieves (0.60 g). The mixture was cooled to −20° C. for 15 min before methanesulfonyl chloride (0.26 mL, 3.34 mmol, 1.75 eq.) was added neat. The flask was sealed and stored at 0° C. for 6 h prior to concentration in vacuo. Purification of the residue by flash chromatography on silica gel (elution with tetrahydrofuran/dichloromethane/methanol, 68:30:2) gave an enriched fraction (280 mg, 24%) containing the title compound as well as a small amount of other closely-spaced by-products which was carried on directly. Potassium phthalimide (0.45 g, 2.43 mmol) was added in one portion to a stirred solution of 2,10-difluoro-12,13-dihydro-12-[6-O-(methylsulfonyl)-β-D-glucopyranosyl]-5H-indolo[2,3-a]pyrrolo[3,4-c]carbazole-5,7(6H)-dione (200 mg, 0.33 mmol) in anhydrous dimethylformamide (10 mL) before the mixture was heated to 130°0 C. for 3 h, cooled to ambient temperature, and concentrated down in vacuo overnight. The residue was then taken up in ethyl acetate (some tetrahydrofuran was added) and washed with 0.1N hydrochloric acid and brine. Following drying and solvent concentration, the residue was purified by flash chromatography on silica gel (elution with 7% methanol in chloroform) to yield 2,10-difluoro-12,13-dihydro-12-[6-deoxy-6-(phthalimido)-β-D-glucopyranosyl]-5H-indolo[2,3-a]pyrrolo[3,4-c]carbazole-5,7(6H)-dione (46 mg, 21%) as a yellow solid as well as the title compound (22 mg, 13%, 2 steps) also as a yellow solid.

For title compound: M.p. >300° C.: $^1$H NMR (500 MHz, DMSO-$d_6$) δ 11.21 (s, 1H), 11.10 (br s, 1H), 9.15 (dd, J=8.7, 5.9 Hz, 1H), 9.05 (dd, J=9.0, 5.8 Hz, 1H), 7.47 (d, J=9.4 Hz, 1H), 7.42 (d, J=10.2 Hz, 1H), 7.31 (dt, J=9.0, 2.2 Hz, 1H), 7.24 (dt, J=9.2, 2.2 Hz, 1H), 6.97 (d, J=7.7 Hz, 1H), 6.39 (br s, 1H), 5.87 (br s, 1H), 4.60 (s, 2H), 4.44 (d, J=7.2 Hz, 1H), 4.17 (m, 1H), 4.07–4.02 (m, 2H); IR (KBr, cm$^{-1}$) 3414, 1747, 1700, 1623, 1580, 1452, 1386, 1327, 1230, 1167, 1114, 1055, 1021, 760; HRMS (neg ESI, M−H$^-$) calc'd for $C_{26}H_{16}F_2N_3O_6$ 505.1086, obsd 504.1029.

EXAMPLE 15

2,3,9,10-Tetrafluoro-12-(2-O-benzyl-3,6-anhydro-4-deoxy-β-D-glucopyranosyl)-6,7,12,13-tetrahydro (5H)indolo[2,3-a]pyrrolo[3,4-c]carbazole-5,7-dione:

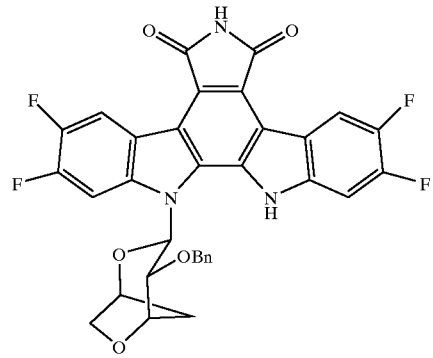

To a solution of 2,3,9,10-tetrafluoro-12-(2-O-benzyl-4-deoxy-β-D-glucopyranosyl)-6,7,12,13-tetrahydro(5H) indolo[2,3-a]pyrrolo[3,4-c]carbazole-5,7-dione (0.018 g, 0.028 mmol) in 0.5 mL of dry pyridine was added a solution of triphenylphosphine (0.022 mg, 0.084 mmol) in 0.1 mL of dry pyridine and then diisopropyl azodicarboxylate (DIAD) (0.017 mL, 0.084 mmol) was added dropwise at room temperature under Ar. The resulting blood-red mixture was stirred at room temperature under Ar for 16 h and then it was quenched by adding water (0.1 mL), followed by methanol (0.1 mL). This mixture was evaporated in vacuo and the residue was purified using preparative tlc (4×20×20 cm plates, 0.5 mm SiO$_2$/CH$_2$Cl$_2$-MeCN, 9:1) to give the title compound (0.007 g, 41%) as a bright yellow solid: $^1$H NMR (THF-$d_8$, 400 MHz) δ10. 83 (br s, 1H), 10.08 (br s, 1H), 9.12 (dd, J=11.0, 8.6 Hz, 1H), 9.02 (dd, J=11.0, 8.4 Hz, 1H), 7.72 (m, 1H), 7.36 (m, 1H), 6.83 (t, J=7.4 Hz, 1H), 6.70 (t, J=7.6 Hz, 2H), 6.59 (d, J=7.6 Hz, 2H), 6.23 (d, J=7.4 Hz, 1H), 4.93 (s, 1H), 4.76 (d, J=6.0 Hz, 1H), 4.41 (d, J=11.7 Hz, 1H), 4.31 (d, J=8.9 Hz, 1H), 4.29 (d, J=10.2 Hz, 1H), 4.13 (d, J=11.7 Hz, 1H), 3.87 (d, J=9.2 Hz, 1H), 3.10 (d, J=13.4 Hz, 1H), 2.10 (dd, J=13.4, 6.0 Hz); MS (ESI$^-$) m/e 614 (M−H)$^-$.

EXAMPLE 16

2,3,9,10-Tetrafluoro-12-(3,6-anhydro-4-deoxy-β-D-glucopyranosyl)-6,7,12,13-tetrahydro(5H)indolo[2,3-a]pyrrolo[3,4-c]carbazole-5,7-dione

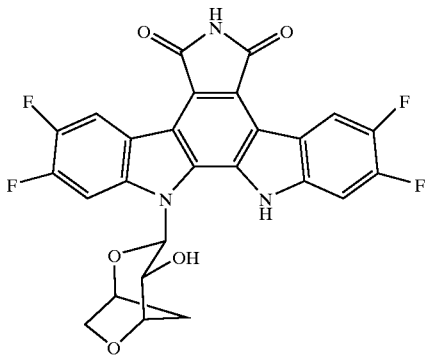

A mixture of 2,3,9,10-tetrafluoro-12-(2-O-benzyl-3,6-anhydro-4-deoxy-β-D-glucopyranosyl)-6,7,12,13-tetrahydro(5H)indolo[2,3-a]pyrrolo[3,4-c]carbazole-5,7- dione (0.034 g, 0.055 mmol) and 20% Pd(OH)$_2$/C (0.048 g) in 5 mL of freshly distilled THF was hydrogenated (balloon pressure) at room temperature for 5 days. The resulting mixture was filtered through a bed of Celite and the cake was washed with THF and then with methanol. The filtrate was evaporated and the residue was chromatographed (Sephadex LH-20/methanol) to give the title compound (0.017 g, 59%) as a yellow solid: $^1$H NMR (THF-d$_8$, 400 MHz) δ 11.15 (br s, 1H), 10.17 (br s, 1H), 9.19 (dd, J=11.1, 8.5 Hz, 1H), 9.09 (dd, J=11.2, 8.3 Hz, 1H), 7.81 (dd, J=11.6, 6.7 Hz, 1H), 7.51 (dd, 10.5, 6.7 Hz, 1H), 6.21 (d, J=7.3 Hz, 1H), 5.37 (br s, 1H), 4.89 (s, 1H), 4.57 (m, 2H), 4.27 (d, J=9.7 Hz, 1H), 3.85 (d, J=9.1 Hz, 1H), 3.09 (d, J=13.4 Hz, 1H), 2.09 (dd, J=13.1, 6.0 Hz, 1H); MS (ESI$^-$) m/e 524 (M–H)$^-$; HPLC: 99.0% (270 nm).

EXAMPLE 17

2,3,9,10-Tetrafluoro-12-(3,6-anhydro-4-deoxy-4,4-difluoro-β-D-glucopyranosyl)-6,7,12,13-tetrahydro(5H)indolo[2,3-a]pyrrolo[3,4-c]carbazole-5,7-dione

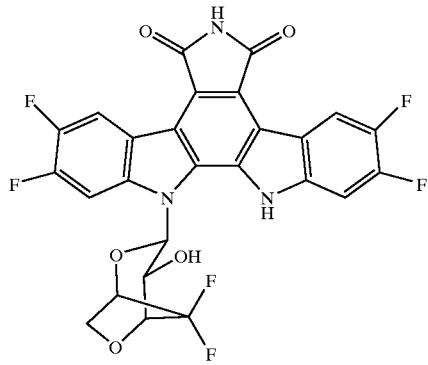

To a solution of 2,3,9,10-tetrafluoro-12-(4-deoxy-4,4-difluoro-β-D-glucopyranosyl)-6,7,12,13-tetrahydro(5H) indolo[2,3-a]pyrrolo[3,4-c]carbazole-5,7-dione (0.035 g, 0.060 mmol) in 4 mL of dry THF was added triphenylphosphine (0.048 g, 0.18 mmol) and DIAD (0.035 mL, 0.18 mmol), at room temperature under Ar. The resulting reddish-orange solution was stirred at room temperature for 18 h and then it was partitioned with ethyl acetate-water. The organic phase was separated, washed (brine), dried (Na$_2$SO$_4$) and evaporated to give a yellow gum. This residue was purified by prep. tlc (20×20 cm×0.5 mm SiO$_2$/THF-hexane, 1:1) and the major fraction was repurified by prep. hplc to give the title compound (0.009 g, 29%) as a yellow solid: $^1$H NMR (acetone-d$_6$, 400 MHz) δ 10.67 (s, 1H), 9.83 (s, 1H), 8.88 (m, 1H), 8.73 (m, 1H), 7.56 (m, 2H), 6.44 (m, 1H), 4.91 (m, 2H), 4.47 (d, J=10.0 Hz, 1H), 4.41(d, J=11.0 Hz, 1H), 4.27 (m, 1H); MS (ESI$^-$) m/e 560 (M–H)$^-$; HPLC: 91.1% (320 nm).

EXAMPLE 18

3,9-Difluoro-12,13-dihydro-13-[(3,6-anhydro)-β-D-galactopyranosyl]-5H-indolo[2,3-a]pyrrolo[3,4-c]carbazole-5,7(6H)-dione:

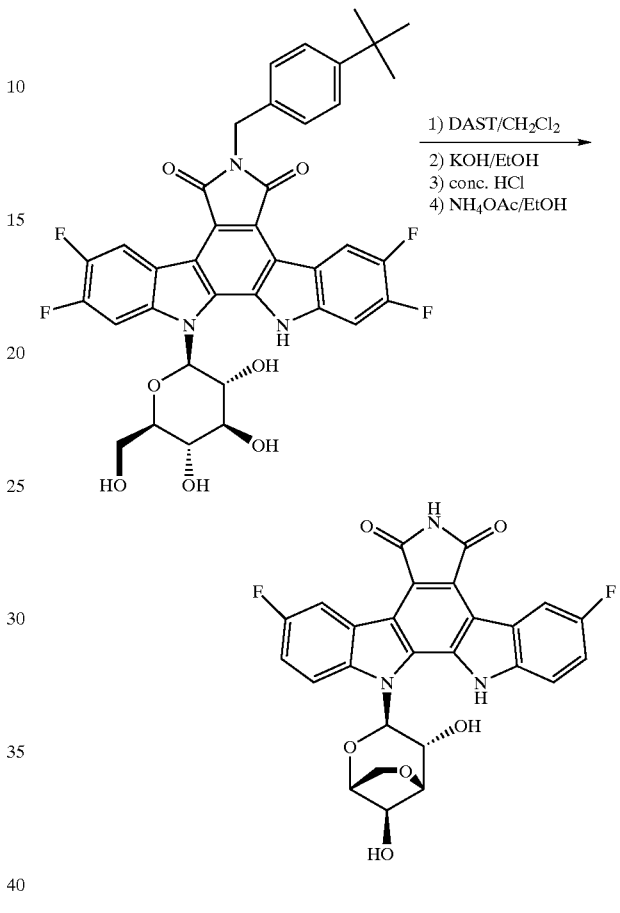

(Diethylamino)sulfur trifluoride (1.02 ml, 7.72 mmol) was added to a stirred suspension of 3,9-difluoro-12,13-dihydro-13-[β-D-glucopyranosyl]-5H-indolo[2,3-a]pyrrolo[3,4-c] carbazole-5,7(6-N-(4-t-butyl)benzyl)-dione (1.01 g, 1.51 mmol) in 50 ml anhydrous CH$_2$Cl$_2$ at −50° C. and the reaction mixture stirred for 3.5 hours during while temperature rose to +15° C. The mixture was cooled to −78° C., quenched by addition of 5 ml CH$_3$OH and poured on 1N HCl. The crude product was extracted with ethyl acetate, the organic layers were washed with saturated aqueous NaHCO$_3$-solution and brine and dried over Na$_2$SO$_4$ and concentrated in vacuo.

The resulting crude product was dissolved in 100 ml Ethanol and 10 ml 3.83 M aqueous KOH was added. The mixture was stirred at room temperature for 17 hours under argon after which 10 ml conc. aqueous HCl was added and stirring continued for an additional 30 minutes. To this was added 150 g NH$_4$OAc and an additional 200 ml ethanol and the mixture heated to reflux for 3 days. The reaction was poured on saturated aqueous NaHCO$_3$-solution and extracted with ethyl acetate. The organic layers were washed with water and brine and dried over Na$_2$SO$_4$ and concentrated in vacuo.

Flash column chromatography on silica gel using a gradient from 100% chloroform to 4% methanol in chloroform followed by Sephadex LH-20 purification in methanol gave 22.0 mg of the title compound: 500 MHz $^1$H-NMR ($d_6$-DMSO) δ 12.76 (bs, 1H), 11.15 (bs, 1H), 8.90 (dd, J=2.6, 9.6 Hz, 1H), 8.75 (dd, J=2.6, 9.8 Hz, 1H), 7.95 (m, 1H), 7.67 (m, 1H), 7.44 (m, 2H), 6.32 (d, J=8.3 Hz, 1H), 5.35 (d, J=4.6 Hz, 1H), 4.68 (s, 1H), 4.60 (m, 1H), 4.58 (m, 2H), 4.41 (d, J=8 Hz, 1H), 4.28 (d, J=5.6 Hz, 1H), 4.16 (d, J=9.3 Hz, 1H); IR (KBr, cm$^{-1}$) 3616, 3444, 3246, 2995, 1747, 1698, 1619, 1587, 1481, 1395, 1328, 1290, 1246, 1189; ESI (NEG) mass spectrum, m/e 504 (M−H$^-$); HRMS (FAB, M+H$^+$) m/z$_{(obs.)}$=506.11676 m/z$_{(calc.)}$=506.116748.

The title compound represents one of the major relevant products isolated from this reaction sequence.

Biological Activity

The compounds of the present invention are useful pharmacologic agents with anti-tumor properties. With topoisomerase I active properties, the compounds can be useful as anti-tumor agents. In recent years, numerous reports have appeared in the literature suggesting that the role of topoisomerase I targeting drugs is to stabilize a covalent DNA-topoisomerase I complex to yield enzyme-linked DNA single-strand breaks. From a pharmacologic standpoint, there are advantages to target Topoisomerase I. First, its occurrence at relatively high levels in both proliferating and quiescent cells suggests that its function may be independent of cellular growth rate. Second, topoisomerase I active agents may be effective in slow-growing as well as rapidly proliferating tumors. Cells from colon tumors have been shown to contain higher intracellular levels of topoisomerase I than normal mucosal cells, suggesting the possibility for a selective cytotoxic advantage. Thus, inhibition of proliferation of tumor cells by compounds of the present invention compounds was initially demonstrated by effective inhibition of human topoisomerase I. Selected compounds of the present invention, usually having EC$_{50}$ values less than 10 µM in the topoisomerase I assay, were also tested in an inhibition of human/mouse tumor cell proliferation assay.

Topoisomerase I Activity (In Vitro)

Topoisomerase I activity was measured as described below: The procedure for assaying compound-induced, topoisomerase I-mediated single strand breaks in DNA was essentially that described by Hsiang, et al., (J. Biol. Chem. 1985, 260,14873–14878). Samples dissolved in 100% DMSO as either 10 µM or 10 mg/ml solutions, unless otherwise stated, were diluted in Tris-EDTA buffer. Marine bacteriophage PM2 DNA (Boehringer Mannheim) was also diluted in Tris-EDTA buffer to a concentration of 0.02 µg/µl. Different dilutions of compound being evaluated were mixed with diluted DNA and this mixture was added to 1000 unit (one unit of enzyme activity is defined as the amount capable of relaxing 100 ng of supercoiled DNA in approximately 30 minutes at 37° C.) aliquots of purified human topoisomerase I (Topogen) in 2×reaction buffer to start the reaction. The compound—DNA—enzyme mixture was incubated for 30 minutes at 37° C. before stopping the reaction with warm stop buffer containing sodium dodecyl sulfate and proteinase K (Sigma). These mixtures were allowed to incubate at 37° C. for another 10 minutes, at which time the mixtures were removed from the waterbath and extracted with a 24:1 mixture of chloroform/isoamyl alcohol. Following centrifugation, aliquots of the aqueous phases were placed in wells of a 0.9% agarose (SeaKem) gel in Tris-borate buffer containing 0.5 µg/ml of ethidium bromide and subjected to electrophbresis for 15 hours to separate the different topological isomers and nicked and broken DNAs. After destaining the gel in water, the ethidium bromide stained DNA reaction products were visualized by exposing the gel to UV irradiation. Negatives of photographs of the irradiated gels were scanned with a densitometer and areas under the peaks were calculated in order to obtain percent-single strand DNA break formation for each sample. A median effective concentration(EC$_{50}$) was obtained for each compound by interpolation between points of the resulting dose-effect curve which defines the potency of the compound for its effect in inducing topoisomerase I-mediated single strand breaks in DNA.

The topoisomerase I activity for selected compounds of the present invention is shown below in Table I.

TABLE I

| Example No. | TOPO I EC$_{50}$ (µM) |
| --- | --- |
| 2 | 0.36 |
| 1 | 0.085 |
| 18 | 0.18 |
| 4 | 0.01 |
| 3 | 0.014 |
| 11 | 0.13 |
| 17 | 15.0 |
| 13 | 0.11 |
| 14 | 5.50 |
| 7 | 0.58 |
| 8 | 0.018 |
| 12 | 0.58 |
| 6 | 0.01 |

In Vitro Cell-Based Cytotoxicity Activity

The proliferation inhibition activity against murine P388 cell line was measured as follow. Cytotoxicity was assessed in HCT116 human colon carcinoma cells by XTT (2,3-bis(2-methoxy-4-nitro-5-sulfophenyl)-5-[(phenylamino)carbonyl]-2H-tetrazolium hydroxide assay as described in the literature by Scudiero, D A, Shoemaker, R H, Paull, K D, Monks, A, Tierney, S, Nofziger, T H, Currens, M J, Seniff, D, and Boyd, M R. Evaluation of a soluble tetrazolium/formazan assay for cell growth and drug sensitivity in culture using human and other tumor cell lines, was done according to the procedure described in Cancer Res. 48: 4827–4833, 1988. Cells were plated at 4000 cells/well in 96 well microtiter plates and 24 hrs later drugs were added and serial-diluted. The cells were incubated at 37° C. for 72 hrs at which time the tetrazolium dye, XTT, containing phenazine methosulfate was added. A dehydrogenase enzyme in live cells reduoes the XTT to a form that absorbs light at 450 nm which can be quantitated spectrophotometrically. The greater the absorbance the greater the number of live cells. The results are expressed as an IC50 which is the drug concentration required to inhibit cell proliferation (i.e. absorbance at 450 nm) to 50% of that of untreated control cells.

The results for selected compounds of the present invention are shown in Table II.

TABLE II

| Example No. | P388 IC$_{50}$ (µM) |
| --- | --- |
| 2 | 0.0388 |
| 1 | 0.093 |
| 18 | 0.1233 |

TABLE II-continued

| Example No. | P388 IC$_{50}$ ($\mu$M) |
| --- | --- |
| 4 | <0.003 |
| 3 | 0.0146 |
| 11 | 0.07 |
| 17 | 0.24 |
| 13 | 0.0232 |
| 14 | 6.22 |
| 16 | 0.31 |
| 7 | 0.4928 |
| 8 | 0.0053 |
| 12 | 0.1066 |
| 6 | 0.0141 |

What is claimed is:

1. A compound according to the formula:

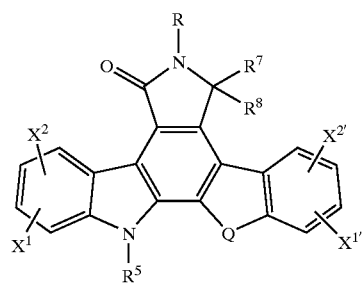

(I)

or a stereoisomer or pharmaceutically acceptable salt or solvate thereof, useful for inhibiting topoisomerase I and the proliferation of tumor cells, wherein:

R is hydrogen, OH, OC$_{1-7}$alkyl, NH$_2$, N(C$_{1-3}$alkyl)$_2$ or C$_{1-7}$alkyl, wherein said C$_{1-7}$alkyl is optionally substituted with one or more substituents selected from the group consisting of halogen, CN, OR$^9$ and NR$^9$R$^{10}$;

Q is O, S, CH$_2$ or NR$^{5a}$;

R and R$^{5a}$ are each independently selected from the group consisting of:

hydrogen, Formula (B), Formula (C), and Formula (D):

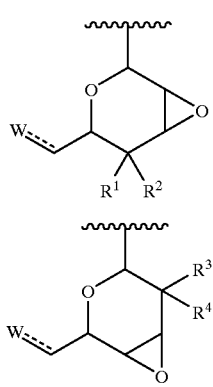

(B)

(C)

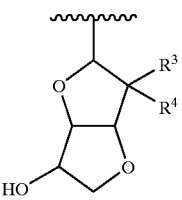

(D)

provided that:

if Q is NR$^{5a}$, then one of R$^5$ and R$^{5a}$ must be hydrogen and the other must be one of Formula (B), Formula (C), and Formula (D);

R$^1$, R$^2$ R$^3$ and R$^4$ are each independently selected from the group consisting of: hydrogen, C$_{1-7}$alkyl, C$_{3-7}$cycloalkyl, halogen, azido, NR$^9$R$^{10}$, NHC(O)NR$^9$R$^{10}$, NHC(O)OR$^9$, C(O)OR$^9$, SR$^9$, and OR$^9$, wherein said C$_{1-7}$alkyl is optionally substituted with one or more substituents selected from the group consisting of halogen, CN, OR$^9$ SR$^9$ and NR$^9$R$^{10}$;

or R$^1$ and R$^2$ together form =N—OH, =O or —NR$^9$R$^{10}$;

or R$^3$ and R$^4$ together form =N—OH, =O or —NR$^9$R$^{10}$;

W is selected from the group consisting of hydrogen, C$_{1-7}$alkyl, C$_{3-7}$cycloalkyl, halogen, azido, NR$^9$R$^{10}$, NHC(O)NR$^9$R$^{10}$, NHC(O)OR$^9$, N—OH, O and OR$^9$, wherein said C$_{1-7}$alkyl is optionally substituted with one or more substituents selected from the group consisting of halogen, CN, OR$^9$ and NR$^9$R$^{10}$;

R$^7$ and R$^8$ are each independently OH or H or together form =O;

R$^9$ and R$^{10}$ are each independently selected from the group consisting of: hydrogen, C$_{1-7}$alkyl and C$_{3-7}$cycloalkyl, wherein said C$_{1-7}$alkyl is optionally substituted with one or more substituents selected from the group consisting of halogen, CN, OH, O—C$_{1-7}$alkyl, NH$_2$ and N(C$_{1-3}$alkyl)$_2$; or R$^9$ and R$^{10}$ together with the nitrogen atom to which they are attached form a non-aromatic 5–8 membered heterocycle containing one or two of the same or different heteroatoms selected from the group consisting of O, N and S; and X$^1$, X$^{1'}$, X$^2$, and X$^{2'}$ are each independently selected from the group consisting of hydrogen, halogen, cyano, OR$^9$, —CF$_3$, alkylcarbonly, C$_{1-7}$alkyl, nitro, NR$^9$R$^{10}$, SR$^9$ and C(O)OR$^9$; wherein said C$_{1-7}$alkyl is optionally substituted with one or more substituents selected from the group consisting of halogen, CN, OR$^9$, SR$^9$ and NR$^9$R$^{10}$.

2. A compound according to claim 1, wherein R$^{5a}$ is not H.

3. A compound according to claim 1, wherein R$^{5a}$ is formula (C).

4. A compound according to claim 1, wherein R$^5$ is formula (B).

5. A compound according to claim 1, wherein R$^5$ is formula (C).

6. A compound according to claim 1, wherein R$^5$ is formula (D).

7. A compound according to claim 1, wherein Q is NR$^{5a}$.

8. A compound according to claim 7, wherein R$^{5a}$ is H.

9. A compound according to claim 1, wherein Q is S.

10. A compound according to claim 1, wherein R is H, OH or NH$_2$.

11. A compound according to claim 1, wherein R is H.

12. A compound according to claim 1, wherein $R^7$ and $R^8$ together are =O.

13. A compound according to claim 1, wherein $X^{2'}$ and $X^2$ are each F and $X^1$ and $X^{1'}$ are each H.

14. A compound according to claim 1, Wherein $X^2$ is F and $X^{2'}$, $X^1$ and $X^{1'}$ are each H.

15. A compound according to claim 1, wherein $X^{2'}$ is F and $X^2$, $X^1$ and $X^{1'}$ are each H.

16. A compound according to claim 1, wherin $X^{2'}$, $X^2$, $X^1$ and $X^{1'}$ are each F.

17. A compound according to claim 1, wherein $X^{2'}$ and $X^2$ are each H and $X^1$ and $X^{1'}$ are each F.

18. A compound according to claim 1, wherein $R^1$, $R^2$, $R^3$ and $R^4$ are each independently selected from the group consisting of H, F and $OR^9$ wherein $R^9$ is H.

19. A compound according to claim 1, wherein W is fluorine.

20. A compound according to claim 1, wherein the bond attaching $R^5$ to N is in the β designation when $R^5$ is not hydrogen.

21. A compound according to claim 1, wherein the bond attaching $R^{5a}$ to N is in the β designation when $R^{5a}$ is not hydrogen.

22. A compound according to claim 1, wherein the bond attaching $R^5$ to N is in the α designation when $R^5$ is not hydrogen.

23. A compound according to claim 1, wherein the bond attaching $R^{5a}$ to N is in the α designation when $R^5$ is not hydrogen.

24. A pharmaceutical composition comprising:
   a compound of Formula (I) as defined in claim 1 or a stereoisomer or a pharmaceutically acceptable salt or a solvate thereof; and
   a pharmaceutical carrier.

* * * * *